US008053451B2

(12) United States Patent
Munoz et al.

(10) Patent No.: US 8,053,451 B2
(45) Date of Patent: Nov. 8, 2011

(54) HYDROXYBENZOATE SALTS OF METANICOTINE COMPOUNDS

(75) Inventors: Julio A. Munoz, Walnut Cove, NC (US); John Genus, Winston-Salem, NC (US); James R. Moore, Newark, DE (US)

(73) Assignee: Targacept, Inc., Winston-Salem, NC (US)

( * ) Notice: Subject to any disclaimer, the term of this patent is extended or adjusted under 35 U.S.C. 154(b) by 337 days.

(21) Appl. No.: 12/264,288

(22) Filed: Nov. 4, 2008

(65) Prior Publication Data

US 2009/0062321 A1    Mar. 5, 2009

Related U.S. Application Data

(63) Continuation of application No. 11/270,018, filed on Nov. 9, 2005, now Pat. No. 7,459,469.

(60) Provisional application No. 60/626,751, filed on Nov. 10, 2004.

(51) Int. Cl.
*C07D 213/62* (2006.01)
*C07D 213/78* (2006.01)
*A01N 43/40* (2006.01)
*A61K 31/44* (2006.01)

(52) U.S. Cl. .................................. 514/351; 546/300

(58) Field of Classification Search .............. 546/300; 514/351
See application file for complete search history.

(56) References Cited

U.S. PATENT DOCUMENTS

| | | | |
|---|---|---|---|
| 4,192,946 A | 3/1980 | Clauson-Kaas et al. |
| 4,487,607 A | 12/1984 | Rose et al. |
| 4,582,823 A | 4/1986 | Heffner et al. |
| 4,922,901 A | 5/1990 | Brooks et al. |
| 5,013,753 A | 5/1991 | Casagrande et al. |
| 5,073,547 A | 12/1991 | Casagrande et al. |
| 5,187,166 A | 2/1993 | Kikuchi et al. |
| 5,212,188 A | 5/1993 | Caldwell et al. |
| 5,583,140 A | 12/1996 | Bencherif et al. |
| 5,597,919 A | 1/1997 | Dull et al. |
| 5,604,231 A | 2/1997 | Smith |
| 5,616,707 A | 4/1997 | Crooks et al. |
| 5,616,716 A | 4/1997 | Dull et al. |
| 5,663,356 A | 9/1997 | Ruecroft et al. |
| 5,672,601 A | 9/1997 | Cignarella |
| 5,726,316 A | 3/1998 | Crooks |
| 5,811,442 A | 9/1998 | Ben et al. |
| 5,852,041 A | 12/1998 | Cosford et al. |
| 5,861,423 A | 1/1999 | Caldwell |
| 6,232,316 B1 | 5/2001 | Dull et al. |
| 6,337,351 B1 | 1/2002 | Dull et al. |
| 6,432,954 B1 | 8/2002 | Dull et al. |
| 6,492,399 B1 | 12/2002 | Dull et al. |
| 6,599,897 B1 | 7/2003 | Brown |
| 6,603,011 B1 | 8/2003 | Caldwell et al. |
| 6,632,823 B1 | 10/2003 | Vernier et al. |
| 6,743,812 B1 | 6/2004 | Dull |
| 6,958,399 B2 | 10/2005 | Caldwell et al. |
| 7,459,469 B2 | 12/2008 | Munoz et al. |
| 2002/0016460 A1 | 2/2002 | Snow et al. |
| 2002/0052497 A1 | 5/2002 | Caldwell et al. |
| 2003/0069272 A1 | 4/2003 | Yerxa et al. |
| 2004/0044023 A1 | 3/2004 | Cantillon et al. |
| 2004/0067974 A1 | 4/2004 | Czollner et al. |
| 2005/0203130 A1 | 9/2005 | Buntinx |
| 2006/0024358 A1 | 2/2006 | Santini et al. |
| 2006/0062838 A1 | 3/2006 | Dipierro et al. |
| 2006/0122237 A1 | 6/2006 | Munoz et al. |
| 2006/0122238 A1 | 6/2006 | Dull et al. |
| 2006/0159768 A1 | 7/2006 | Brown |
| 2007/0265314 A1 * | 11/2007 | Dull et al. ............... 514/349 |
| 2008/0085888 A1 | 4/2008 | Breining et al. |
| 2008/0249142 A1 | 10/2008 | Dull et al. |
| 2009/0062321 A1 | 3/2009 | Munoz et al. |

FOREIGN PATENT DOCUMENTS

| | | |
|---|---|---|
| EP | 0297858 | 1/1989 |
| EP | 0516409 | 12/1992 |
| GB | 2295387 | 5/1996 |
| JP | 70012732 | 11/1967 |
| JP | 2002518373 | 6/2002 |
| JP | 2008519768 | 6/2008 |
| WO | 9212122 | 7/1992 |
| WO | 9408992 | 4/1994 |
| WO | 9534555 | 12/1995 |
| WO | 9631475 | 10/1996 |
| WO | 9640682 | 12/1996 |
| WO | 9740011 | 10/1997 |
| WO | 9850367 | 11/1998 |
| WO | 9921834 | 5/1999 |
| WO | 99/65876 | * 12/1999 |
| WO | 9965876 | 12/1999 |

(Continued)

OTHER PUBLICATIONS

Canney et al., Life sciences, (1998) vol. 63, No. 24, pp. PL329-PL336.*

Grottick et al., "Effect of subtype selective nicotinic compounds on attention as assessed by the five-choice serial reaction time task," Behav Brain Res. (2000) 117:197-208.

de Costa et al., "Synthesis and biological evaluation of conformationally restricted 2-(1-pyrrolidinyl)-N-[2-(3,4-dichlorophenyl)ethyl]-N-methylethylenediamines as sigma receptor ligands. 1. Pyrrolidine, piperidine, homopiperidine, and tetrahydroisoquinoline classes," J med Chem (1992) 35(23):4334-4343.

(Continued)

*Primary Examiner* — D M Seaman
*Assistant Examiner* — Niloofar Rahmani

(57) ABSTRACT

Patients susceptible to or suffering from conditions and disorders, such as central nervous system disorders, are treated by administering to a patient in need thereof compositions that are hydroxybenzoate salts of E-metanicotine-type compounds. The formation of hydroxybenzoate salts of the E-metanicotine compounds is also useful in purifying the E-metanicotine compounds, as the hydroxybenzoate salts tend to crystallize out, leaving impurities such as Z-metanicotine compounds, and compounds where the double bond has migrated, in solution. If desired, the hydroxybenzoate salts can be converted to either the free base (the E-metanicotine) or to another pharmaceutically acceptable salt form.

3 Claims, No Drawings

FOREIGN PATENT DOCUMENTS

| | | |
|---|---|---|
| WO | 0007600 | 2/2000 |
| WO | 2004/031151 A1 | 8/2000 |
| WO | 0075110 | 12/2000 |
| WO | 0117943 | 3/2001 |
| WO | 0178735 | 10/2001 |
| WO | 0205801 A2 | 1/2002 |
| WO | 02078693 | 10/2002 |
| WO | 03051302 | 6/2003 |
| WO | 03082205 | 10/2003 |
| WO | 2005/072742 A1 | 4/2004 |
| WO | 2005063296 A2 | 7/2005 |
| WO | 00/45846 A1 | 8/2005 |
| WO | 2005105729 | 11/2005 |
| WO | 2006053039 A2 | 5/2006 |
| WO | 2006053082 | 5/2006 |
| WO | 2006114400 | 11/2006 |
| WO | 2007134034 | 11/2007 |
| WO | 2007134038 | 11/2007 |
| WO | 2007147014 A2 | 12/2007 |
| WO | 2008034041 | 3/2008 |
| WO | 2008073942 | 6/2008 |
| WO | 2008091588 | 7/2008 |
| WO | 2008091592 | 7/2008 |

OTHER PUBLICATIONS

Koller et al., "The Preparation of Substituted Hydroxyphenyl-pyridyl-ethanols and -Hydroxyphenyl—methylpyridineethanols by the Condensation of 2-, 3-, or 4-Picolyllithium with Select Hydroxybenzaldehydes and 4-Hydroxyacetophenone," Synthetic Communications (1995) 25(19):2963-2974.
Acheson et al., "Transformations involving the Pyrrolidine Ring of Nicotine," J Chem Soc (1980) 1:579-585.
Arneric et al., "Cholinergic channel modulators as a novel therapeutic strategy for Alzheimer's disease," Exp Opin Invest Drugs (1996) 5(1):79-100.
Arneric et al., "Preclinical Pharmacology of ABT-418: A Prototypical Cholinergic Channel Activator for the Potential Treatment of Alzheimer's Disease," CNS Drug Rev (1995) 1(1):1-26.
Ashimori et al., "Novel 1, 4-Dihydropyride Calcium Antagonists. I. Synthesis and Hypotensive Activity of 4-(Substittuted Pyridyl)-1,4-dihydropyridine Derivatives" Chem. Pharm Bull (1990) 38(9):2446-2458.
Bannon et al., "Broad-Spectrum, Non-Opioid Analgesic Activity by Selective Modulation of Neuronal Nicotinic Acetylcholine Receptors," Science (1998) 279:77-81.
Batkowski, Rocz Chem (1967) 41:729-741.
Bencherif et al., "Targeting Neuronal Nicotinic Receptors: a Path to New Therapies," Current Drug Targets (2002) 1 (4):349-357.
Bencherif et al., "RJR-2403: A Nicotinic Agonist with CNS Selectivity I: In Vitro characterization," J Pharmacol Exper Therapeutics (1996) 279(3):1413-1421.
Borch "Reductive Amination with Sodium Cyanoborohydride: N, N-Dimethylcyclohexyl," Org Syn (1974) 52:124-127.
Brioni et al., "The harmacology of (−)-Nicotine and Novel Cholinergic channel Modulators," Adv Pharmacol (1997) 37:153-214.
Cai et al., "5-(N-Oxyaza-7-substituted-1,4-dihydroquinoxaline-2,3-diones: Novel, Systemically Active and Broad Spectrum An," J Med Chem (1997) 40(22):3679-3686.
Cheng et al., "Relationship Between the Inhibition Constant (KI) and the Concentration of Inhibitor which Causes 50 Per Cent inhibition (I50) of an Enzymatic Reaction," (1973) Biochem Pharmacol (1973) 22(23):3099-3108.
Chiari et al., "Sex Differences in Cholinergic Analgesia I: A Supplemental Nicotinic Mechanism in Normal Females," (1999) Anesthesiology 91(5):1447-1454.
Comins et al., "Lithiation of Methoxypyridines Directed by beta-Amino Alkoxides," (1990) J Org Chem 91(5):69-73.
Dallacker et al., "," Naturforsch (1979) 34b:1729-1736.
Damaj et al., "Analgesic Activity of Metanicotine, A Selective Nicotinic Agonist," Neuroscience (1997) 23:669.
Damaj et al., "Antinociceptive and Pharmacological Effects of Metanicotine, a Selective Nicotinic Agonist," J Pharmacol Exp Ther (1999) 291(1):390-398.
Decina et al., "Cigarette Smoking and Neuroleptic-Induced Parkinsonism," Biol Psychiatry (1990) 28(6):502-508.
Dubey et al., "Synthesis & Spectra of 2-Alkyl—& 6-Bromo-2-alkyl-1H-imidazo[b]pyridines," Indian J Chem (1978) 16B (6):531-533.
Dwoskin et al., "Recent developments in neuronal nicotinic acetylcholine receptor antagonists," Exp Opin Ther Patents (2000) 10(10):1561-1581.
Frank et al., "Palladium-Catalyzed Vinylic Substitution Reactions with Heterocyclic Bromides," J Org Chem (1978) 43 (15):2947-2949.
Frissen et al., "Ring-Transformations of Pyrimidines by Intramolecular Diels-Alder Reactions, Sythesis of Annelated Pyridines," Tetrahedron (1989) 45(3):803-812.
Gibson et al., "Principal Components Describing biological Activities and Molecular Diversity of Heterocyclic Aromatic Ring Fragments," J Med Chem (1996) 39:4065-4072.
Greco et al., "Synthese of Some Substituted Pyridylsydnones," J Heterocyclic Chem (1970) 7:761-766.
Hall et al., "Effects of Nicotine on the Release of 3H-Noradrenaline from the Hypothalamus," Biochemical Pharmacology (1972) 21:1829-1838.
Hamon "Neuropharmacology of anxiety: perspectives and prospects," TIPS (1994) 15:36-39.
Harsing et al., "Dopamine Efflux from Striatun After Chronic Nicotine: Evidence for Autoreceptor Desensitization," J Neurochem (1992) 59(1):48-54.
Hayes et al., Elimination of Dihydrogen from Collision-activated Alkoxide Negative Ions in the Gas Phase. An Ab inition and Isotope Effect Study, J Chem Soc Chem Commun (1984) 21:1431-1432.
Hertog et al., "The Reactivity of Bromine Atoms in Brominated Pyridines," Recl Tray Chim Pays-Bas (1948) 67 (7/8):377-379.
Hery et al., "Control of the release of newly synthetized 3H-5-Hydroxytryptamine by Nicotinic and Muscarinic Receptors in Rat Hypothalamic Slices," Naunyn-Schmiedeberg's Arch Pharmacol (1977) 296:91-97.
Holladay et al., "Neuronal Nicotinic Acetylcholine Receptors as Targets for Drug Discovery," J Med Chem (1997) 40 (26):4169-4194.
Hoyer et al., "Partial agonists, full agonists, antagonists: dilemmas of definition," TIPS Reviews (1993) 14:270-275.
Hughes et al., "S 40 Nicitine and Neuropsychiatric Disorders," Session 6, in International Symposium on Nicotine: The Effects of Nicotine on Biological Systems II, (Birkhauser Verlag Publishers, 1994).
Ishihara et al., "Zinc Bromide Promoted Allylatin of Aluminum Acetals Derived from Perfluoro Carboxylic Acid Esters and Diisobutylaluminum Hybride," Tetrahedron Letters (1993) 34(36):5777-5780.
Kalivretenos et al., "Synthesis of Beta-Resocylic Macrolides via Organopalladium Chemistry Application to the Total Synthesis of (S)-Zearalenone," J Org Chem (1991) 56:2883-2894.
Koch et al., "Chemistry of 3-Hydroxypyridine Part 2: Synthesis of 5,6 -Dihalo-3-hydroxypyriines," Synthesis (1990) 499-501.
Kubota et al., "Facile Synthesis of Beta-Trifluoromethlated Alcohols from Trifluoroacetaldehyde Ethyl Hemiacetal," Tetrahedron Letters (1992) 33(10):1351-1354.
Kuhler et al., "Structure-Activity Relationship of Omeprazole and Analogues as Helicobacter pylorie Urease lnhibitors," J Med Chem (1995) 38:4906-4916.
LaForge "The preparation and properties of some new derivatives of pyridine," J Am Chem Soc (1928) 50:2477-2483.
Lavand'homme et al., "Sex Differences in Cholinergic Analgesia II: differing Mechanisms in Two Models of Allodynia," Anesthesiology (1999) 91(5):1455-1461.
Levin et al., "Nicotinic treatment for cognitive dysfunction," Current Drug Targets: CNS and Neurological Disorders (2002) 1(4):423-431.
Lippiello et al., "RJR-2403: a nicotinic agonist with CNS selectivity II. In vivo characterization," J Pharmacol Exp Ther (1996) 279(3):1422-1429.
Loffer et al., "[Uber die bildung des i-nicotins aus N-methyl-b-pyridyl-butyl-amin (dihydrometanicotin)]," Chem Ber (1909) 42:3431-3438.
Malek et al., "Palladium-catalyzed synthesis of cinnamylamines," J Org Chem (1982) 47:5395-5397.

Michael et al., "Synthesis of functionalized cyclopentanes, cyclohexanes and cycloheptanes by a silicon-induced domino reaction," Liebigs Ann (1996) 11:1811-1821.

Morisawa et al., "Modification at 5-position of 4-deoxypyridoxol and alpha4-norpyridoxol," Agr Biol Chem (1975) 39 (6):1275-1281.

Onaivi et al., "Chronic nicotine reverses age-associated increases in tail-flick latency and anxiety in rats," Life Sciences (1993) 54(3):193-202.

O'Neill et al., "The role of neuronal nicotinic acetylcholine receptors in acute and chronic neurodegeneration," Current Drug Targets: CNS and Neurological Disorders (2002) 1(4):399-411.

Paulder et al., "1,2,4-Triazines. III. A convenient synthesis of 1,2,4-triazines and their covalent hydration," J Heterocyclic Chem (1970) 7:767-771.

Pomerleau et al., "The effects of cigarette smoking on pain and anxiety," Addictive Behaviors (1984) 9(3):265-271.

Pullan et al., "Transdermal nicotine for active ulcerative colitis," New England J Med (1994) 330(12):811-815.

Rapier et al., "Stereoselective nicotine-induced release of dopamine from striatal synaptosomes: concentration dependence and repetitive stimulation," J Neurochem (1988) 50(4):1123-1130.

Rondahl "Synthetic analogues of nicotine VI 1,2. Nicotine substituted in the 5-position," Acta Pharmaceutica Suecica (1977) 14(2):113-118.

Rowell et al., "Nicotinic stimulation of [3H]acetylcholine release from mouse cerebral cortical synaptosomes," J Neurochem (1984) 43(6):1593-1598.

Sanberg et al., "Nicotine potentiation of haloperidol-induced catalepsy: striatal mechanisms," Pharmacol Biochem & Behavior (1993) 46(2):303-307.

Sandor et al., "Effect of nicotine on dopaminergic-cholinergic interaction in the striatum," Brain Res (1991) 567 (2):313-316.

Sjak-Shie et al., "Effects of chronic nicotine and pilocarpine administration on neocortical neuronal density and [3H] GABA uptake in nucleus basalis lesioned rats," Brain Res (1993) 624:295-298.

Schmitt et al., "Chapter 5. Targeting nicotinic acetylcholine receptors: advances in molecular design and therapies," Ann Rep Med Chem (2000) 35:41-51.

Taylor et al., "Intramolecular diels-alder reactions of 1,2,4-triazines. A general synthesis of furo[2,3- ]pyridines, 2,3-dihydropyrano[2,3- ]pyridines, and pyrrolo[2,3- ]pyridines," Tetrahedron (1987) 43(21):5145-5158.

Toth et al., "Effect of nicotine of extracellular levels of neurotransmitters assessed by microdialysis in various brain regions: role of glutamic acid," Neurochem Res (1992) 17(3):265-270.

Tripathi et al., "Nicotine-induced antinociception in rats and mice: correlation with nicotine brain levels," J Pharmacol Exp Ther (1982) 221(1):91-96.

Viaud et al., "Synthesis of 6-substituted 2-phenyloxazolo-[4,5-b]pyridines," Heterocycles (1995) 41(12):2799-2809.

Vizi et al., "Acetylcholine release from guinea-pig ileum by parasympathetic ganglion stimulants and gastrin-like polypeptides," Br J Pharmac (1973) 47(4):765-777.

Wagner et al., "Does smoking reduce the risk of neuroleptic parkinsonoids?" Pharmacopsychiat (1988) 21:302-303.

Williams et al., "Neuronal nicotinic acetylcholine receptors," Drug News Perspec (1994) 7(4):205-223.

Yoshikawa et al., "Synthesis of 3-pyridinols. II. Reaction of 4-methyloxazole with dienophiles," Chem Pharm Bull (1965) 13(7):873-878.

Bibliographic printout from DIALOG research company (corresponding to Japanese Patent No. 70012732).

Office Action dated Jan. 7, 2008 cited in copending U.S. Appl. No. 11/270,018.

Notice of Allowance dated Apr. 8, 2008 cited in copending U.S. Appl. No. 11/270,753.

Geerts "Ispronicline Targacept," Current Opinion in Investigational Drugs (2006) 7(1):60-69.

Buccafusco "Neuronal nicotinic receptor subtypes: defining therapeutic targets," Molecular Interventions (2004) 4 (5):285-295.

Haberman "Nicotinic receptor agonists for treating diseases of cognitive dysfunction," Spectrum (2007) pp. 11-1 to 11-19.

Notice of Allowance for co-pending U.S. Appl. No. 11/270,018 dated Aug. 4, 2008.

Office Action for co-pending U.S. Appl. No. 11/855,175 dated Nov. 13, 2008.

Gould "Salt selection for basic drugs," International Journal of Pharmaceutics (1986) 33:201-217.

Bastin, et al., Salt Selection and Optimization for Pharmaceutical New Chemical Entities, Organic Process Research and Development, 2000; 4(5):427-435.

Levin, et al., Nicotine-Haloperidoal Interactions and Cognitive Performance in Schizophrenics, Neuropsychopharmacology, 1996;15(5):429-436.

Ichikawa, et al., Atypical antipsychotic drugs, quetiapine, iloperidone, and melperone, preferentially increase dopamine and acetylcholine release in rat medial prefrontal cortex: role of 5-HT1A receptor agonism, Brain Research (2002) 956:349-357.

Shoemaker, et al., Quetiapine produces a prolonged reversal of the sensorimotor gating-disruptive effects of basolateral amygdala lesions in rats, Behavioral Neuroscience (2003) 117(1):136-143.

Supplemental Notice of Allowability for co-pending U.S. Appl. No. 11/270,753 dated May 16, 2008.

Notice of Allowance for co-pending U.S. Appl. No. 11/270,753 dated Oct. 24, 2008.

Official Action for co-pending U.S. Appl. No. 11/745,682 dated Dec. 11, 2009.

Final Office Action received in copending U.S. Appl. No. 11/745,682 dated May 3, 2010.

Letchworth et al., "Tc-1734: an orally active neuronal nicotinic receptor modulator with long-lasting cognitive effects, anti-depressant effects, and neuroprotective activity," Society for Neuroscience (2003) Abstract.

Advisory Action dated Oct. 8, 2010 received in copending U.S. Appl. No. 11/745,682.

Berge et al., "Pharmaceutical Salts," (1977) J Pharma Sci 66(1):1-19.

Non-final office action dated Dec. 15, 2010 received in copending U.S. Appl. No. 12/299,925.

Notice of Allowance dated May 12, 2011 received in copending U.S. Appl. No. 12/299,925.

* cited by examiner

US 8,053,451 B2

HYDROXYBENZOATE SALTS OF METANICOTINE COMPOUNDS

This application claims benefit of U.S. Provisional Patent Application No. 60/626,751, filed Nov. 10, 2004, the contents of which are fully incorporated herein by reference.

FIELD OF THE INVENTION

The present invention relates to processes for preparing nicotinic compounds and pharmaceutically acceptable salts thereof, as well as pharmaceutical compositions and methods for treating a wide variety of conditions and disorders associated with dysfunction of the central and autonomic nervous systems.

BACKGROUND OF THE INVENTION

Nicotine has been proposed to have a number of pharmacological effects. See, for example, Pullan et al., *N. Engl. J. Med.* 330:811-815 (1994). Certain of those effects can be related to effects upon neurotransmitter release. Release of acetylcholine, dopamine, norepinephrine, serotonin, and glutamate upon administration of nicotine has been reported (Rowell et al., *J. Neurochem.* 43:1593 (1984); Rapier et al., *J. Neurochem.* 50:1123 (1988); Sandor et al., *Brain Res.* 567: 313 (1991); Vizi, *Br. J. Pharmacol.* 47:765 (1973); Hall et al., *Biochem. Pharmacol.* 21:1829 (1972); Hery et al., *Arch. Int. Pharmacodyn. Ther.* 296:91 (1977); and Toth et al., *Neurochem Res.* 17:265 (1992)). Confirmatory reports and additional recent studies have included the modulation in the Central Nervous System (CNS) of glutamate, nitric oxide, GABA, takykinins, cytokines, and peptides (reviewed in Brioni et al., *Adv. Pharmacol.* 37:153 (1997)). In addition, nicotine reportedly potentiates the pharmacological behavior of certain pharmaceutical compositions used to treat certain disorders. See, for example, Sanberg et al., *Pharmacol. Biochem. & Behavior* 46:303 (1993); Harsing et al., *J. Neurochem.* 59:48 (1993); and Hughes, *Proceedings from Intl. Symp. Nic.* S40 (1994). Furthermore, the neuroprotective effects of nicotine have been proposed, see, for example, Sjak-shie et al., *Brain Res.* 624:295 (1993). Various other beneficial pharmacological effects have also been proposed. See, for example, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994); Tripathi et al., *J. Pharmacol. Exp. Ther.* 221:91 (1982); and Hamon, *Trends in Pharmacol. Res.* 15:36 (1994).

Various compounds that target nAChRs have been reported as being useful for treating a wide variety of conditions and disorders. See, for example, Williams et al., *DN&P* 7(4):205 (1994); Arneric et al., *CNS Drug Rev.* 1(1):1 (1995); Arneric et al., *Exp. Opin. Invest. Drugs* 5(1):79 (1996); Bencherif et al., *J. Pharmacol. Exp. Ther.* 279:1413 (1996); Lippiello et al., *J. Pharmacol. Exp. Ther.* 279:1422 (1996); Damaj et al., *J. Pharmacol. Exp. Ther.* 291:390 (1999); Chiari et al., *Anesthesiology* 91:1447 (1999); Lavand'homme and Eisenbach, Anesthesiology 91:1455 (1999); Holladay et al., *J. Med. Chem.* 40(28): 4169 (1997); Bannon et al., *Science* 279: 77 (1998); PCT WO 94/08992; PCT WO 96/31475; PCT WO 96/40682; and U.S. Pat. No. 5,583,140 to Bencherif et al.; U.S. Pat. No. 5,597,919 to Dull et al.; U.S. Pat. No. 5,604,231 to Smith et al.; and U.S. Pat. No. 5,852,041 to Cosford et al. Nicotinic compounds are reported as being particularly useful for treating a wide variety of CNS disorders. Indeed, a wide variety of nicotinic compounds have been reported to have therapeutic properties. See, for example, Bencherif and Schmitt, *Current Drug Targets: CNS and Neurological Disorders* 1(4): 349-357 (2002), Levin and Rezvani, *Current Drug Targets: CNS and Neurological Disorders* 1(4): 423-431 (2002), O'Neill, et al., *Current Drug Targets: CNS and Neurological Disorders* 1(4): 399-411 (2002), U.S. Pat. No. 5,1871,166 to Kikuchi et al., U.S. Pat. No. 5,672,601 to Cignarella, PCT WO 99/21834 and PCT WO 97/40049, UK Patent Application GB 2295387 and European Patent Application 297,858.

CNS disorders are a type of neurological disorder. CNS disorders can be drug-induced; can be attributed to genetic predisposition, infection or trauma; or can be of unknown etiology. CNS disorders comprise neuropsychiatric disorders, neurological diseases, and mental illnesses, and include neurodegenerative diseases, behavioral disorders, cognitive disorders, and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of acetylcholine, dopamine, norepinephrine, and/or serotonin.

Relatively common CNS disorders include pre-senile dementia (early-onset Alzheimer's disease), senile dementia (dementia of the Alzheimer's type), micro-infarct dementia, AIDS-related dementia, vascular dementia, Creutzfeld-Jakob disease, Pick's disease, Parkinsonism including Parkinson's disease, Lewy body dementia, progressive supranuclear palsy, Huntington's chorea, tardive dyskinesia, hyperkinesia, epilepsy, mania, attention deficit disorder, anxiety, dyslexia, schizophrenia, depression, obsessive-compulsive disorders, and Tourette's syndrome.

Subtypes of nAChRs are present in both the central and peripheral nervous systems, but the distribution of subtypes is heterogeneous. For instance, the subtypes which are predominant in vertebrate brain are $\alpha 4\beta 2$, $\alpha 7$, and $\alpha 3\beta 2$, whereas those which predominate at the autonomic ganglia are $\alpha 3\beta 4$ and those of neuromuscular junction are $\alpha 1\beta 1\delta\gamma$ and $\alpha 1\beta 1\delta\epsilon$ (see for instance Dwoskin et al., *Exp. Opin. Ther. Patents* 10: 1561 (2000); and Schmitt and Bencherif, *Annual Reports in Med. Chem.* 35: 41 (2000)).

A limitation of some nicotinic compounds is that they elicit various undesirable pharmacological effects because of their interaction with nAChRs in peripheral tissues (for example, by stimulating muscle and ganglionic nAChR subtypes). It is therefore desirable to have compounds, compositions, and methods for preventing and/or treating various conditions or disorders (e.g., CNS disorders), including alleviating the symptoms of these disorders, where the compounds exhibit nicotinic pharmacology with a beneficial effect on the CNS nAChRs (e.g., upon the functioning of the CNS), but without significant associated effects on the peripheral nAChRs (compounds specific for CNS nAChRs). It is also highly desirable to have compounds, compositions, and methods that affect CNS function without significantly affecting those receptor subtypes which have the potential to induce undesirable side effects (e.g., appreciable activity at cardiovascular and skeletal muscle sites).

Methods for treating and/or preventing the above-described conditions and disorders by administering E-metanicotine compounds, particularly those which maximize the effect on CNS function without significantly affecting those receptor subtypes which have the potential to induce undesirable side effects, have been described in the art. Representative E-metanicotine compounds for use in treating and/or preventing the above-described disorders are disclosed, for example, in U.S. Pat. No. 5,212,188 to Caldwell et al., U.S. Pat. No. 5,604,231 to Smith et al., U.S. Pat. No. 5,616,707 to Crooks et al.; U.S. Pat. No. 5,616,716 to Dull et al., U.S. Pat. No. 5,663,356 to Ruecroft et al., U.S. Pat. No. 5,726,316 to Crooks et al., U.S. Pat. No. 5,811,442 to Bencherif et al., U.S. Pat. No. 5,861,423 to Caldwell et al., PCT WO 97/40011; PCT WO 99/65876 PCT WO 00/007600; and U.S. patent application Ser. No. 09/391,747, filed on Sep. 8, 1999, the contents of each of which are hereby incorporated by reference.

The syntheses described in the art for forming E-metanicotines typically involve performing a Heck reaction between a halogenated heteroaryl ring, such as a halo-pyridine or halo-pyrimidine, and a double bond-containing compound. The double bond-containing compound typically includes either a hydroxy group, which is converted to an amine group to form the E-metanicotine, or includes a protected amine group, which is deprotected following the Heck reaction to form the E-metanicotine. A limitation of the Heck coupling chemistry is that, while the major reaction product is the desired E-metanicotine, there are minor reaction products, including the Z-metanicotine, a metanicotine compound where the double bond has migrated from the position adjacent to the heteroaryl (such as pyridine or pyrimidine) ring (i.e., a non-conjugated double bond), and a compound in which the heteroaryl group is attached at the secondary (as opposed to primary) alkene carbon (i.e., a methylene compound or "exo" double bond). It can be difficult to remove these minor reaction products, particularly on scale-up.

It would be advantageous to provide new methods of preparing purified E-metanicotine compounds substantially free from the above-described minor reaction products. It would also be advantageous to provide new salt forms of these drugs to improve their bioavailability, and/or to assist in preparing large quantities of these compounds in a commercially reasonable manner. The present invention provides such new synthesis methods and new salt forms.

SUMMARY OF THE INVENTION

New methods of synthesizing E-metanicotine compounds are described herein, as well as new pharmaceutically acceptable salt forms of E-metanicotine compounds. Pharmaceutical compositions including the new salt forms, and methods of treatment and/or prevention using the new salt forms, are also disclosed.

The methods for synthesizing the E-metanicotine compounds typically include the step of performing a Heck reaction between a halogenated heteroaryl ring, such as a halo-pyridine or halo-pyrimidine, and a double bond-containing compound. The double bond-containing compound typically includes either a hydroxy group, which is subsequently converted to an amine group to form the E-metanicotine compound, or includes a protected amine group, which is deprotected following the Heck reaction to form the E-metanicotine compound.

After the Heck reaction and formation of an E-metanicotine with a free amine group (whether by conversion of a hydroxy group or deprotection of a protected amine group), the next step involves forming a hydroxybenzoate salt of the E-metanicotine compound. Under certain conditions, one can precipitate out the hydroxybenzoate salt of the E-metanicotine compound while leaving the minor impurities (Z-metanicotine and/or the isomers of the E-metanicotine compound wherein the double bond has migrated to a position other than directly adjacent to the heteroaryl ring or wherein the attachment of the aryl group to the alkene chain is at the secondary double bond carbon) in solution. This improvement makes it relatively easy to remove these minor reaction products, particularly on scale-up.

In one embodiment, the synthesis of the E-metanicotines involves forming an amine-protected 4-penten-2-amine intermediate, and coupling this intermediate via a Heck reaction with a halogenated heteroaryl ring. The choice of heteroaryl ring is not essential to the success of the Heck coupling reaction, although pyridine and pyrimidine rings can be preferred. (2S)-(4E)-N-methyl-5-[3-(5-isopropoxypyridin)yl)]-4-penten-2-amine is a representative E-metanicotine, p-hydroxybenzoate is a representative hydroxybenzoate salt, and (2S)-(4E)-N-methyl-5-[3-(5-isopropoxypyridin)yl)]-4-penten-2-amine p-hydroxybenzoate is a representative E-metanicotine hydroxybenzoate salt.

An exemplary reaction is shown below:

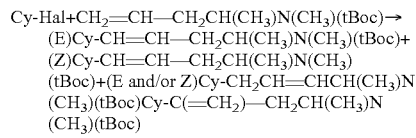

where Cy is a five or six membered heteroaryl ring.

In another embodiment, the Heck coupling reaction takes place using a hydroxy-alkene, such as 4-penten-2-ol, and the hydroxy group is converted to an amine group after the Heck coupling reaction takes place. The conversion can be effected, for example, by converting the hydroxy group to a tosylate, and displacing the tosylate with a suitable amine, such as methylamine. In this embodiment, the Heck coupling reaction still forms the same major and minor products, except that they include a hydroxy group rather than a protected amine group. Following formation of the amine-containing compound (i.e., the (E)-metanicotine), if the impurities (i.e., the minor products of the Heck coupling reaction) are not already removed, the chemistry involved in forming the hydroxybenzoate salts is substantially the same.

After deprotecting the amine group (in the first embodiment), or forming the amine group (in the second embodiment), one can form a hydroxybenzoate salt of the E-metanicotine by reaction with a hydroxybenzoic acid as described herein. The hydroxybenzoate salts of the major product (the (E)-metanicotine) and of the minor products will form. However, under certain conditions, the hydroxybenzoate salt of the major reaction product, the (E)-metanicotine hydroxybenzoate salt, will precipitate out of solution in relatively pure form, leaving behind a mother liquor enriched in the minor impurities. This result comprises a significant advance in the synthesis and purification of (E)-metanicotines.

In one embodiment, the hydroxybenzoate salts are isolated and then used as intermediates to form different salt forms by reaction with different pharmaceutically acceptable acids or salts thereof. However, in another embodiment, the E-metanicotine hydroxybenzoate salts are used as active pharmaceutical ingredients (API's). The hydroxybenzoate salts can be used directly, or included in pharmaceutical compositions by combining them with a pharmaceutically acceptable excipient. The hydroxybenzoate salts and/or pharmaceutical compositions can be used to treat and/or prevent a wide variety of conditions or disorders. The disorders are particularly those disorders characterized by dysfunction of nicotinic cholinergic neurotransmission, including disorders involving neuromodulation of neurotransmitter release, such as dopamine release. The compounds can be used in methods for treatment and/or prophylaxis of disorders, such as central nervous system (CNS) disorders, which are characterized by an alteration in normal neurotransmitter release. The compounds can also be used to treat certain conditions (e.g., a method for alleviating pain). The methods involve administering to a subject an effective amount of a E-metanicotine hydroxybenzoate salt, or pharmaceutical composition including a E-metanicotine hydroxybenzoate salt, as described herein.

The pharmaceutical compositions, when employed in effective amounts, can interact with relevant nicotinic receptor sites in a patient, and act as therapeutic and/or prophylactic agents in connection with a wide variety of conditions and disorders, particularly CNS disorders characterized by an alteration in normal neurotransmitter release. The pharmaceutical compositions can provide therapeutic benefit to individuals suffering from such disorders and exhibiting clinical manifestations of such disorders in that the compounds within those compositions, when employed in effective amounts, can (i) exhibit nicotinic pharmacology and affect relevant nicotinic receptors sites (e.g., activate nicotinic receptors), and (ii) modulate neurotransmitter secretion, and hence prevent and suppress the symptoms associated with those disorders. In addition, the compounds can (i) increase the number of nicotinic cholinergic receptors of the brain of the patient, (ii) exhibit neuroprotective effects and (iii) when employed in effective amounts can exhibit relatively low levels of adverse side effects (e.g., significant increases in blood pressure and heart rate, significant negative effects upon the gastro-intestinal tract, and significant effects upon skeletal muscle).

The foregoing and other aspects of the present invention are explained in detail in the detailed description and examples set forth below.

DETAILED DESCRIPTION OF THE INVENTION

The hydroxybenzoate salts described herein, which are derived from E-metanicotines and hydroxybenzoic acids, have a number of advantages over other salts derived from E-metanicotines and other acids. In general, the hydroxybenzoic acid salts of E-metanicotines are water-soluble materials that tend to be highly crystalline and less hygroscopic in nature than other salts. For example, the p-hydroxybenzoate salt of (2S)-(4E)-N-methyl-5-[3-(5-isopropoxypyridin)yl)]-4-penten-2-amine is physically and chemically stable, free-flowing, crystalline powder. Such properties are definite advantages for pharmaceutical formulation development and pharmaceutical manufacturing. If necessary, this salt can be milled to an acceptable particle size range for pharmaceutical processing. The salt is compatible with a wide range of excipients that might be chosen for the manufacture of solid oral dosage forms. This is especially so for those exicipients, such as polysaccharide derivatives, that are pharmaceutically defined hydrates and those with only loosely bound surface water. As an illustration, salts derived from certain E-metanicotines, such as E-metanicotine and fumaric acid are prone to the formation of impurities within the salt. For example, impurities arise from the Michael addition reaction of the secondary amine in E-metanicotine to the olefin in fumaric acid. These impurities lower the chemical purity of the salt and adversely affect the chemical integrity of the salt upon long-term storage.

The synthetic methods described herein will be better understood with reference to the following preferred embodiments. The following definitions will be useful in defining the scope of the invention:

As used herein, "aromatic" refers to 3 to 10, preferably 5 and 6-membered ring aromatic and heteroaromatic rings.

As used herein, "aromatic group-containing species" refer to moieties that are or include an aromatic group. Accordingly, phenyl and benzyl moieties are included in this definition, as both are or include an aromatic group.

As used herein, "aryl" refers to aromatic radicals having six to ten carbon atoms, such as phenyl, naphthyl, and the like; "substituted aryl" refers to aryl radicals further bearing one or more substituent groups as defined herein.

As used herein, "alkylaryl" refers to alkyl-substituted aryl radicals; "substituted alkylaryl" refers to alkylaryl radicals further bearing one or more substituent groups as defined herein; "arylalkyl" refers to aryl-substituted alkyl radicals; and "substituted arylalkyl" refers to arylalkyl radicals further bearing one or more substituent groups as defined herein.

As used herein, $C_{1-6}$ alkyl radicals (lower alkyl radicals) contain from 1 to 6 carbon atoms in a straight or branched chain, and also include $C_{3-6}$ cycloalkyl moieties and alkyl radicals that contain $C_{3-6}$ cycloalkyl moieties.

As used herein, "alkenyl" refers to straight chain or branched hydrocarbon radicals including $C_{1-8}$, preferably $C_{1-5}$ and having at least one carbon-carbon double bond; "substituted alkenyl" refers to alkenyl radicals further bearing one or more substituent groups as defined herein.

As used herein, $C_{1-6}$ alkoxy radicals contain from 1 to 6 carbon atoms in a straight or branched chain, and also include $C_{3-6}$ cycloalkyl and alkoxy radicals that contain $C_{3-6}$ cycloalkyl moieties.

As used herein, aryl radicals are selected from phenyl, naphthyl, and indenyl.

As used herein, cycloalkyl radicals are saturated or unsaturated cyclic ring-containing radicals containing three to eight carbon atoms, preferably three to six carbon atoms; "substituted cycloalkyl" refers to cycloalkyl radicals further bearing one or more substituent groups as defined herein.

As used herein, halogen is chlorine, iodine, fluorine, or bromine.

As used herein, heteroaryl radicals contain from 3 to 10 members, preferably 5 or 6 members, including one or more heteroatoms selected from oxygen, sulfur, and nitrogen. Examples of suitable 5-membered ring heteroaryl moieties include furyl, thiophenyl, pyrrolyl, imidazolyl, oxazolyl, thiazolyl, thienyl, tetrazolyl, and pyrazolyl. Examples of suitable 6-membered ring heteroaryl moieties include pyridinyl, pyrimidinyl, and pyrazinyl, of which pyridinyl and pyrimidinyl are preferred.

As used herein, "heterocyclyl" refers to saturated or unsaturated cyclic radicals containing one or more heteroatoms (e.g., O, N, S) as part of the ring structure and having two to seven carbon atoms in the ring; "substituted heterocyclyl" refers to heterocyclyl radicals further bearing one or more substituent groups as defined herein. Examples of suitable heterocyclyl moieties include, but are not limited to, piperidinyl, morpholinyl, pyrrolidinyl, imidazolidinyl, pyrazolidinyl, isothiazolidinyl, thiazolidinyl, isoxazolidinyl, oxazolidinyl, piperazinyl, tetrahydropyranyl, and tetrahydrofuranyl.

As used herein, polycycloalkyl radicals are fused cyclic ring structures. Representative polycycloalkyl radicals include, but are not limited to, adamantyl, bornanyl, norbornanyl, bornenyl, and norbornenyl. Polycycloalkyl radicals can also include one or more heteroatoms, such as N, O, or S.

As used herein, cycloalkyl radicals contain from 3 to 8 carbon atoms. Examples of suitable cycloalkyl radicals include, but are not limited to, cyclopropyl, cyclobutyl, cyclopentyl, cyclohexyl, cycloheptyl, and cyclooctyl.

As used herein, the term "substituted" as used with any of the above terms, refers to the presence of one, two or three substituents such as alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, NR'R", CF$_3$, CN, NO$_2$, C$_2$R', SH, SCH$_3$, N$_3$, SO$_2$ CH$_3$, OR', (CR'R")$_q$OR', O—(CR'R")$_q$C$_2$R', SR', C(=O) NR'R", NR'C(=O)R", C(=O)R', C(=O)OR', OC(=O)R', (CR'R")$_q$OCH$_2$C$_2$R', (CR'R")$_q$C(=O)R', (CR'R")$_q$C (CHCH$_3$)OR', O(CR'R")$_q$C(=O)OR', (C R'R")$_q$C(=O) NR'R", (CR'R")$_q$NR'R", CH=CHR', OC(=O)NR'R", and NR'C(=O)OR" where q is an integer from 1 to 6 and R' and R" are individually hydrogen, or alkyl (e.g., C$_{1-10}$ alkyl, preferably C$_{1-5}$ alkyl, and more preferably methyl, ethyl, isopropyl, tertiarybutyl or isobutyl), cycloalkyl (e.g., cyclopropyl cyclobutyl, cyclopentyl, cyclohexyl, cycloheptyl, and adamantyl), a non-aromatic heterocyclic ring wherein the heteroatom of the heterocyclic moiety is separated from any other nitrogen, oxygen or sulfur atom by at least two carbon atoms (e.g., quinuclidinyl, pyrollidinyl, and piperidinyl), an aromatic group-containing species (e.g., pyridinyl, quinolinyl, pyrimidinyl, furanyl, phenyl, and benzyl where any of the foregoing can be suitably substituted with at least one substituent group, such as alkyl, hydroxyl, alkoxyl, halo, or amino substituents).

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" is a substance that provides a level of stimulation to its binding partner that is intermediate between that of a full or complete antagonist and an agonist defined by any accepted standard for agonist activity. It will be recognized that stimulation, and hence, inhibition is defined intrinsically for any substance or category of substances to be defined as agonists, antagonists, or partial agonists. As used herein, "intrinsic activity", or "efficacy," relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. See Hoyer, D. and Boddeke, H., *Trends Pharmacol Sci.* 14(7):270-5 (1993). Where such contextually specific evaluations are relevant, and how they might be relevant in the context of the present invention, will be apparent to one of ordinary skill in the art.

As used herein, neurotransmitters whose release is mediated by the compounds described herein include, but are not limited to, acetylcholine, dopamine, norepinephrine, serotonin, and glutamate, and the compounds described herein function as agonists or partial agonists at one or more of the Central Nervous System (CNS) nAChRs.

I. Compounds

The compounds described herein are hydroxybenzoate salts of (E)-metanicotine-type compounds.

A. Hydroxybenzoic Acids

The hydroxybenzoic acids that can be used to prepare the hydroxybenzoate salts of the (E)-metanicotine-type compounds have the following general formula:

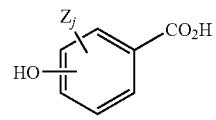

where the hydroxy group can be present in a position ortho, meta or para to the carboxylic acid group, Z represents a non-hydrogen substituent, and j is a number from zero to three, representing the number of Z substituents that can be present on the ring. Examples of suitable Z substituents include alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, NR'R", CF$_3$, CN, NO$_2$, C$_2$R', SH, SCH$_3$, N$_3$, SO$_2$ CH$_3$, OR', (CR'R")$_q$OR', O—(CR'R")$_q$C$_2$R', SR', C(=O)NR'R", NR'C (=O)R", C(=O)R', C(=O)OR', OC(=O)R', (CR'R")$_q$ OCH$_2$C$_2$R', (CR'R")$_q$C(=O)R', (CR'R")$_q$C(CHCH$_3$)OR', O(CR'R")$_q$C(=O)OR', (CR'R")$_q$C(=O)NR'R", (CR'R")$_q$ NR'R", CH=CHR', OC(=O)NR'R", and NR'C(=O)OR" where q is an integer from 1 to 6 and R' and R" are individually hydrogen, or alkyl (e.g., C$_{1-10}$ alkyl, preferably C$_{1-5}$ alkyl, and more preferably methyl, ethyl, isopropyl, tertiarybutyl or isobutyl), cycloalkyl (e.g., cyclopropyl cyclobutyl, cyclopentyl, cyclohexyl, cycloheptyl, and adamantyl), a non-aromatic heterocyclic ring wherein the heteroatom of the heterocyclic moiety is separated from any other nitrogen, oxygen or sulfur atom by at least two carbon atoms (e.g., quinuclidinyl, pyrollidinyl, and piperidinyl), an aromatic group-containing species (e.g., pyridinyl, quinolinyl, pyrimidinyl, furanyl, phenyl, and benzyl where any of the foregoing can be suitably substituted with at least one substituent group, such as alkyl, hydroxyl, alkoxyl, halo, or amino substituents). Other representative aromatic ring systems are set forth in Gibson et al., *J. Med. Chem.* 39:4065 (1996). R' and R" can be straight chain or branched alkyl, or R' and R" and the intervening atoms can combine to form a ring structure (e.g., cyclopropyl cyclobutyl, cyclopentyl, cyclohexyl, cycloheptyl, adamantyl or quinuclidinyl). The hydroxybenzoic acids can optionally be substituted with a chiral functional group, which can assist in purifying E-metanicotines which contain a chiral carbon, by forming diastereomers.

Representative benzoic acids that can be used include salicylic acid, meta-hydroxybenzoic acid, para-hydroxybenzoic acid, vanillic acid, isovanillic acid, gentisic acid, gallic acid, 5-aminosalicylic acid, syringic acid, 4-methylsalicylic acid, 3-chloro-4-hydroxybenzoic acid, and 5-hydroxyisophthalic acid.

B. E-Metanicotines

The E-metanicotine compounds include compounds of the formulas:

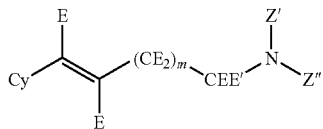

wherein:

Cy is a 5- or 6-membered heteroaryl ring,

E and E' individually represent hydrogen, alkyl, substituted alkyl, halo substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl;

Z' and Z" individually represent hydrogen or alkyl (including cycloalkyl), and preferably at least one of Z' and Z is hydrogen, and most preferably Z' is hydrogen and Z is methyl; alternatively Z', Z", and the associated nitrogen atom can form a ring structure such as aziridinyl, azetidinyl, pyrrolidinyl, piperidinyl, piperazinyl, morpholinyl, and both E groups on the double bond are preferably hydrogen, and m is 1, 2, 3, 4, 5, or 6.

In one embodiment, all of E and E' are hydrogen, and in another embodiment, at least one of E or E' is alkyl and the remaining E and E' are hydrogen. In a preferred embodiment, E' is an alkyl group, preferably a methyl group.

Isomers, mixtures, including racemic mixtures, enantiomers, diastereomers and tautomers of these compounds, as well as pharmaceutically acceptable salts thereof, are also within the scope of the invention.

In one embodiment, Cy is a six-membered ring heteroaryl depicted as follows:

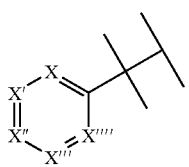

wherein each of X, X', X", X"', and X"" is individually nitrogen, nitrogen bonded to oxygen (e.g., an N-oxide or N—O functionality), or carbon bonded to H or a non-hydrogen substituent species. No more than three of X, X', X", X"', and X"" are nitrogen or nitrogen bonded to oxygen, and it is preferred that only one or two of X, X', X", X"', and X"" are nitrogen or nitrogen bonded to oxygen. In addition, it is highly preferred that not more than one of X, X', X", X"', and X"" is nitrogen bonded to oxygen; and it is preferred that if one of those species is nitrogen bonded to oxygen, that species is X"'. Most preferably, X"' is nitrogen. In certain preferred circumstances, both X' and X"' are nitrogen. Typically, X, X", and X"" are carbon bonded to a substituent species, and it is typical that the substituent species at X, X", and X"" are hydrogen. For certain other preferred compounds where X"" is carbon bonded to a substituent species such as hydrogen, X and X' are both nitrogen. In certain other preferred compounds where X' is carbon bonded to a substituent species such as hydrogen, X and X"' are both nitrogen.

Suitable non-hydrogen substituent species are as defined above with respect to Z.

In another embodiment, Cy is a 5-membered ring heteroaryl of the following formula:

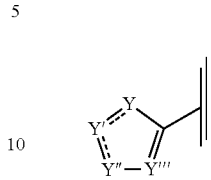

where Y and Y" are individually nitrogen, nitrogen bonded to a substituent species, oxygen, sulfur or carbon bonded to a substituent species, and Y' and Y"' are nitrogen or carbon bonded to a substituent species. The dashed lines indicate that the bonds (between Y and Y' and between Y' and Y") can be either single or double bonds. However, when the bond between Y and Y' is a single bond, the bond between Y' and Y" must be a double bond and vice versa. In cases in which Y or Y" is oxygen or sulfur, only one of Y and Y" is either oxygen or sulfur. At least one of Y, Y', Y", and Y"' must be oxygen, sulfur, nitrogen, or nitrogen bonded to a substituent species. It is preferred that no more than three of Y, Y', Y", and Y"' be oxygen, sulfur, nitrogen, or nitrogen bonded to a substituent species. It is further preferred that at least one, but no more than three, of Y, Y', Y", and Y"' be nitrogen.

Substituent species on X, X', X", X"', X"", Y', Y", and Y"', when adjacent, can combine to form one or more saturated or unsaturated, substituted or unsubstituted carbocyclic or heterocyclic rings containing, but not limited to, ether, acetal, ketal, amine, ketone, lactone, lactam, carbamate, or urea functionalities.

Depending upon the identity and positioning of each individual E and E', certain compounds can be optically active (e.g., the compound can have one or more chiral centers, with R or S configurations). The present invention relates to racemic mixtures of such compounds as well as single enantiomer compounds.

Of particular interest are aryl substituted amine compounds of the formula:

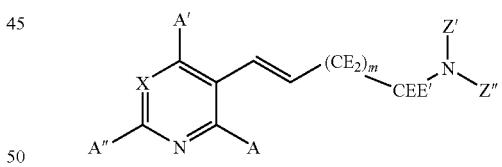

where X', E, E', Z', Z", and m are as defined hereinbefore, and A, A', and A" hydrogen or a substituent species Z as defined above with respect to the hydroxybenzoic acids. Preferably, all E are hydrogen and E' is alkyl, preferably methyl. Preferably, Z' is hydrogen and Z" is hydrogen or methyl. Preferably, m is 1 or 2.

Exemplary types of aryl substituted amine compounds are those of the type set forth in U.S. Pat. No. 5,212,188 to Caldwell et al.; U.S. Pat. No. 5,604,231 to Smith et al.; U.S. Pat. No. 5,616,707 to Crooks et al.; U.S. Pat. No. 5,616,716 to Dull et al.; U.S. Pat. No. 5,663,356 to Ruecroft et al.; U.S. Pat. No. 5,726,316 to Crooks et al.; U.S. Pat. No. 5,811,442 to Bencherif et al.; U.S. Pat. No. 5,861,423 to Caldwell et al.; U.S. Pat. No. 6,337,351 to Dull et al.; WO 97/40011; WO 99/65876; and WO 00/007600. The foregoing references are incorporated herein by reference in their entirety for purposes of providing disclosure of representative compounds useful in carrying out the present invention.

Exemplary compounds useful in accordance with the present invention include metanicotine-type compounds. Representative preferred compounds include (E)-metanicotine, (3E)-N-methyl-4-(5-ethoxy-3-pyridinyl)-3-buten-1-amine, (2S)-(4E)-N-methyl-5-(3-pyridinyl)-4-penten-2-amine, (2R)-(4E)-N-methyl-5-(3-pyridinyl)-4-penten-2-amine, (2S)-(4E)-N-methyl-5-(5-methoxy-3-pyridinyl)-4-penten-2-amine, (2R)-(4E)-N-methyl-5-(5-methoxy-3-pyridinyl)-4-penten-2-amine, (2S)-(4E)-N-methyl-5-(5-isopropoxy-3-pyridinyl)-4-penten-2-amine, (2R)-(4E)-N-methyl-5-(5-isopropoxy-3-pyridinyl)-4-penten-2-amine, (3E)-N-methyl-4-(5-nitro-6-amino-3-pyridinyl)-3-buten-1-amine, (3E)-N-methyl-4-(5-(N-benzylcarboxamido)-3-pyridinyl)-3-buten-1-amine, (2S)-(4E)-N-methyl-5-(5-pyrimidinyl)-4-penten-2-amine, (2R)-(4E)-N-methyl-5-(5-pyrimidinyl)-4-penten-2-amine, (4E)-N-methyl-5-(2-amino-5-pyrimidinyl)-4-penten-2-amine, (4E)-N-methyl-5-(5-amino-3-pyridinyl)-4-penten-2-amine, (2S)-(4E)-N-methyl-5-(5-isopropoxy-1-oxo-3-pyridinyl)-4-penten-2-amine, (3E)-N-methyl-4-(5-isobutoxy-3-pyridinyl)-3-buten-1-amine, (3E)-N-methyl-4-(1-oxo-3-pyridinyl)-3-buten-1-amine, (4E)-N-methyl-5-(1-oxo-3-pyridinyl)-4-penten-2-amine, (3E)-N-methyl-4-(5-ethylthio-3-pyridinyl)-3-buten-1-amine, (4E)-N-methyl-5-(5-trifluoromethyl-3-pyridinyl)-4-penten-2-amine, (4E)-N-methyl-5-(5-((carboxymethyl)oxy)-3-pyridinyl)-4-penten-2-amine, (4E)-5-(5-isopropoxy-3-pyridinyl)-4-penten-2-amine, and (4E)-N-methyl-5-(5-hydroxy-3-pyridinyl)-4-penten-2-amine. Additional representative examples include (2S)-(4E)-N-methyl-5-(5-cyclohexyloxy-3-pyridinyl)-4-penten-2-amine, (2R)-(4E)-N-methyl-5-(5-cyclohexyloxy-3-pyridinyl)-4-penten-2-amine, (2S)-(4E)-N-methyl-5-(5-phenoxy-3-pyridinyl)-4-penten-2-amine, (2R)-(4E)-N-methyl-5-(5-phenoxy-3-pyridinyl)-4-penten-2-amine, (2S)-(4E)-N-methyl-5-(5-(4-fluorophenoxy)-3-pyridinyl)-4-penten-2-amine, (2R)-(4E)-N-methyl-5-(5-(4-fluorophenoxy)-3-pyridinyl)-4-penten-2-amine, (2S)-(4E)-N-methyl-5-(5-(4-chlorophenoxy)-3-pyridinyl)-4-penten-2-amine, (2R)-(4E)-N-methyl-5-(5-(4-chlorophenoxy)-3-pyridinyl)-4-penten-2-amine, (2S)-(4E)-N-methyl-5-(5-(3-cyanophenoxy)-3-pyridinyl)-4-penten-2-amine, (2R)-(4E)-N-methyl-5-(5-(3-cyanophenoxy)-3-pyridinyl)-4-penten-2-amine, (2S)-(4E)-N-methyl-5-(5-(5-indolyloxy)-3-pyridinyl)-4-penten-2-amine, and (2R)-(4E)-N-methyl-5-(5-(5-indolyloxy)-3-pyridinyl)-4-penten-2-amine.

II. Compound Preparation

The manner in which the (E)-metanicotine-type compounds described herein are synthetically produced can vary. For example, the compounds can be prepared by the palladium-catalyzed coupling reaction of an aromatic halide and a terminal olefin containing a protected amine substituent, removal of the protective group to obtain a primary or secondary amine, and optional alkylation to provide a secondary or tertiary amine. In particular, certain metanicotine-type compounds can be prepared by subjecting a 3-halo-substituted, optionally 5-substituted, pyridine compound or a 5-halo-substituted pyrimidine compound to a palladium-catalyzed coupling reaction using an olefin possessing a protected amine functionality (e.g., such an olefin provided by the reaction of a phthalimide salt with 3-halo-1-propene, 4-halo-1-butene, 5-halo-1-pentene or 6-halo-1-hexene). See, Frank et al., *J. Org. Chem.*, 43(15):2947-2949 (1978); and Malek et al., *J. Org. Chem.*, 47:5395-5397 (1982).

In another embodiment, the compounds are synthesized by condensing an olefinic alcohol, such as 4-penten-2-ol, with an aromatic halide, such as 3-bromopyridine or 3-iodopyridine. Typically, the types of procedures set forth in Frank et al., *J. Org. Chem.*, 43: 2947-2949 (1978) and Malek et al., *J. Org. Chem.*, 47: 5395-5397 (1982) involving a palladium-catalyzed coupling of an olefin and an aromatic halide are used. The olefinic alcohol optionally can be protected as a t-butyldimethylsilyl ether prior to the coupling. Desilylation then produces the olefinic alcohol. The alcohol condensation product then is converted to an amine using the type of procedures set forth in deCosta et al., *J. Org. Chem.*, 35: 4334-4343 (1992). Typically, the alcohol condensation product is converted to the aryl substituted olefinic amine by activation of the alcohol using methanesulfonyl chloride or p-toluenesulfonyl chloride, followed by mesylate or tosylate displacement using ammonia, or a primary or secondary amine. Thus, when the amine is ammonia, an aryl substituted olefinic primary amine compound is provided; when the amine is a primary amine such as methylamine or cyclobutylamine, an aryl substituted olefinic secondary amine compound is provided; and when the amine is a secondary amine such as dimethylamine or pyrrolidine, an aryl substituted olefinic tertiary amine compound is provided. Other representative olefinic alcohols include 4-penten-1-ol, 5-hexen-2-ol, 5-hexen-3-ol, 3-methyl-3-buten-1-ol, 2-methyl-3-buten-1-ol, 4-methyl-4-penten-1-ol, 4-methyl-4-penten-2-ol, 1-octen-4-ol, 5-methyl-1-hepten-4-ol, 4-methyl-5-hexen-2-ol, 5-methyl-5-hexen-2-ol, 5-hexen-2-ol and 5-methyl-5-hexen-3-ol. Trifluormethyl-substituted olefinic alcohols, such as 1,1,1-trifluoro-4-penten-2-ol, can be prepared from 1-ethoxy-2,2,2-trifluoro-ethanol and allyltrimethylsilane using the procedures of Kubota et al., *Tetrahedron Letters*, 33(10):1351-1354 (1992), or from trifluoroacetic acid ethyl ester and allyltributylstannane using the procedures of Ishihara et al., *Tetrahedron Letters*, 34(56): 5777-5780 (1993). Certain olefinic alcohols are optically active, and can be used as enantiomeric mixtures or as pure enantiomers in order to provide the corresponding optically active forms of aryl substituted olefinic amine compounds. When an olefinic allylic alcohol, such as methallyl alcohol, is reacted with an aromatic halide, an aryl substituted olefinic aldehyde is produced; and the resulting aldehyde can be converted to an aryl substituted olefinic amine compound by reductive amination (e.g., by treatment using an alkyl amine and sodium cyanoborohydride). Preferred aromatic halides are 3-bromopyridine-type compounds and 3-iodopyridine-type compounds. Typically, substituent groups of such 3-halopyridine-type compounds are such that those groups can survive contact with those chemicals (e.g., tosylchloride and methylamine) and the reaction conditions experienced during the preparation of the aryl substituted olefinic amine compound. Alternatively, substituents such as —OH, —NH$_2$ and —SH can be protected as corresponding acyl compounds, or substituents such as —NH$_2$ can be protected as a phthalimide functionality. In the case of a dihaloaromatic, sequential palladium-catalyzed (Heck-type) couplings to two different olefinic side chains are possible.

In one embodiment, the (E)-metanicotine-type compounds possess a branched side chain, such as (4E)-N-methyl-5-(5-isopropoxy-3-pyridinyl)-4-penten-2-amine. By using one synthetic approach, the latter compound can be synthesized in a convergent manner, in which the side chain, N-methyl-N-(tert-butoxycarbonyl)-4-penten-2-amine is coupled with the 3-substituted 5-halo-substituted pyridine, 5-bromo-3-isopropoxypyridine, under Heck reaction conditions, followed by removal of the tert-butoxycarbonyl protecting group. Typically, the types of procedures set forth in W. C. Frank et al., *J. Org. Chem.* 43:2947 (1978) and N. J. Malek et al., *J. Org.*

*Chem.* 47:5395 (1982) involving a palladium-catalyzed coupling of an olefin and an aromatic halide are used. The required N-methyl-N-(tert-butoxycarbonyl)-4-penten-2-amine can be synthesized as follows: (i) commercially available 4-penten-2-ol (Aldrich Chemical Company, Lancaster Synthesis Inc.) can be treated with p-toluenesulfonyl chloride in pyridine to yield 4-penten-2-ol p-toluenesulfonate, previously described by T. Michel, et al., *Liebigs Ann.* 11: 1811 (1996); (ii) the resulting tosylate can be heated with excess methylamine to yield N-methyl-4-penten-2-amine; (iii) the resulting amine, such as previously mentioned by A. Viola et al., *J. Chem. Soc., Chem. Commun.* 21: 1429 (1984), can be allowed to react with 1.2 molar equivalents of di-tert-butyl dicarbonate in dry tetrahydrofuran to yield the side chain, N-methyl-N-(tert-butoxycarbonyl)-4-penten-2-amine. The halo-substituted pyridine (e.g., 5-bromo-3-isopropoxypyridine), can be synthesized by at least two different routes. In one preparation, 3,5-dibromopyridine is heated at 140° C. for 14 hours with 2 molar equivalents of potassium isopropoxide in dry isopropanol in the presence of copper powder (5%, w/w of the 3,5-dibromopyridine) in a sealed glass tube to yield 5-bromo-3-isopropoxypyridine. A second preparation of 5-bromo-3-isopropoxypyridine from 5-bromonicotinic acid can be performed as follows: (i) 5-Bromonicotinic acid is converted to 5-bromonicotinamide by treatment with thionyl chloride, followed by reaction of the intermediate acid chloride with aqueous ammonia. (ii) The resulting 5-bromonicotinamide, previously described by C. V. Greco et al., *J. Heterocyclic Chem.* 7(4):761 (1970), is subjected to Hofmann degradation by treatment with sodium hydroxide and a 70% solution of calcium hypochlorite. (iii) The resulting 3-amino-5-bromopyridine, previously described by C. V. Greco et al., *J. Heterocyclic Chem.* 7(4): 761 (1970), can be converted to 5-bromo-3-isopropoxypyridine by diazotization with isoamyl nitrite under acidic conditions, followed by treatment of the intermediate diazonium salt with isopropanol to yield 5-bromo-3-isopropoxypyridine. The palladium-catalyzed coupling of 5-bromo-3-isopropoxypyridine and N-methyl-N-(tert-butoxycarbonyl)-4-penten-2-amine is carried out in acetonitrile-triethylamine (2:1, v,v) using a catalyst consisting of 1 mole % palladium(II) acetate and 4 mole % tri-o-tolylphosphine. The reaction can be carried out by heating the components at 80° C. for 20 hours to yield (4E)-N-methyl-N-(tert-butoxycarbonyl)-5-(5-isopropoxy-3-pyridinyl)-4-penten-2-amine. Removal of the tert-butoxycarbonyl protecting group can be accomplished by treatment with 30 molar equivalents of trifluoroacetic acid in anisole at 0° C. to afford (4E)-N-methyl-5-(5-isopropoxy-3-pyridinyl)-4-penten-2-amine. A variety of N-methyl-5-(5-alkoxy or 5-aryloxy-3-pyridinyl)-4-penten-2-amines are available from 3,5-dibromopyridine using this type of technology (i.e., treatment with sodium or potassium alkoxides or aryloxides and subsequent Heck coupling and deprotection).

In another embodiment, a compound such as (4E)-N-methyl-5-(5-methoxy-3-pyridinyl)-4-penten-2-amine can be synthesized by coupling a halo-substituted pyridine, 5-bromo-3-methoxypyridine with an olefin containing a secondary alcohol functionality, 4-penten-2-ol, under Heck reaction conditions; and the resulting pyridinyl alcohol intermediate can be converted to its p-toluenesulfonate ester, followed by treatment with methylamine. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an olefin and an aromatic halide are used. The halo-substituted pyridine, 5-bromo-3-methoxypyridine is synthesized using methodology similar to that described by H. J. den Hertog et al., *Rec. Trav. Chim. Pays-Bas* 67:377 (1948), namely by heating 3,5-dibromopyridine with 2.5 molar equivalents of sodium methoxide in dry methanol in the presence of copper powder (5%, w/w of the 3,5-dibromopyridine) in a sealed glass tube at 150° C. for 14 hours to produce 5-bromo-3-methoxypyridine. The resulting 5-bromo-3-methoxypyridine, previously described by D. L. Comins, et al., *J. Org. Chem.* 55: 69 (1990), can be coupled with 4-penten-2-ol in acetonitrile-triethylamine (1:1:1, v/v) using a catalyst consisting of 1 mole % palladium(II) acetate and 4 mole % tri-o-tolylphosphine. The reaction is carried out by heating the components in a sealed glass tube at 140° C. for 14 hours to yield (4E)-N-methyl-5-(5-methoxy-3-pyridinyl)-4-penten-2-ol. The resulting alcohol is treated with 2 molar equivalents of p-toluenesulfonyl chloride in dry pyridine at 0° C. to produce (4E)-N-methyl-5-(5-methoxy-3-pyridinyl)-4-penten-2-ol p-toluensulfonate. The tosylate intermediate is treated with 120-molar equivalents of methylamine as a 40% aqueous solution, containing a small amount of ethanol as a co-solvent to produce (4E)-N-methyl-5-(5-methoxy-3-pyridinyl)-4-penten-2-amine. When 3,5-dibromopyridine is submitted to Heck coupling with N-methyl-N-(tert-butoxycarbonyl)-4-penten-2-amine, under conditions described above, N-methyl-N-(tert-butoxycarbonyl)-5-(5-bromo-3-pyridinyl)-4-penten-2-amine is produced. This can be coupled in a subsequent Heck reaction with styrene and deprotected (removal of the tert-butoxycarbonyl group), as described previously, to give (4E)-N-methyl-5-[3-(5-trans-beta-styrylpyridin)yl]-4-penten-2-amine. Similar second coupling with ethynylbenzene, and subsequent deprotection, will give (4E)-N-methyl-5-[3-(5-phenylethynylpyridin)yl]-4-penten-2-amine.

Optically active forms of certain aryl substituted olefinic amine compounds, such as (2S)-(4E)-N-methyl-5-(3-pyridinyl)-4-penten-2-amine, can be provided. In one synthetic approach, the latter type of compound is synthesized by coupling a halo-substituted pyridine, 3-bromopyridine, with an olefin possessing a chiral, secondary alcohol functionality, (2R)-4-penten-2-ol, under Heck reaction conditions. The resulting chiral pyridinyl alcohol intermediate, (2R)-(4E)-5-(3-pyridinyl)-4-penten-2-ol is converted to its corresponding p-toluenesulfonate ester, which is subsequently treated with methylamine, resulting in tosylate displacement with inversion of configuration. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an aromatic halide and an olefin are used. The chiral side chain, (2R)-4-penten-2-ol can be prepared by treatment of the chiral epoxide, (R)-(+)-propylene oxide (commercially available from Fluka Chemical Company) with vinylmagnesium bromide and copper(I) iodide in tetrahydrofuran at low temperatures (−25 to −10° C.) using the general synthetic methodology of A. Kalivretenos, J. K. Stille, and L. S. Hegedus, *J. Org. Chem.* 56: 2883 (1991), to afford (2R)-4-penten-2-ol. The resulting chiral alcohol is subjected to a Heck reaction with 3-bromopyridine in acetonitrile-triethylamine (1:1, v/v) using a catalyst consisting of 1 mole % palladium(II) acetate and 4 mole % tri-o-tolylphosphine. The reaction is done by heating the components at 140° C. for 14 hours in a sealed glass tube, to produce the Heck reaction product, (2R)-(4E)-5-(3-pyridinyl)-4-penten-2-ol. The resulting chiral pyridinyl alcohol is treated with 3 molar equivalents of p-toluenesulfonyl chloride in dry pyridine at 0° C., to afford the tosylate intermediate. The p-toluenesulfonate ester is heated with 82 molar equivalents of methylamine as a 40% aqueous solution, containing a small amount of ethanol as a co-solvent, to produce (2S)-(4E)-N-methyl-5-(3-pyridinyl)-4-penten-2-amine.

In a similar manner, the corresponding aryl substituted olefinic amine enantiomer, such as (2R)-(4E)-N-methyl-5-(3-pyridinyl)-4-penten-2-amine, can be synthesized by the Heck coupling of 3-bromopyridine and (2S)-4-penten-2-ol. The resulting intermediate, (2S)-(4E)-5-(3-pyridinyl)-4-penten-2-ol, is converted to its p-toluenesulfonate, which is subjected to methylamine displacement. The chiral alcohol, (2S)-4-penten-2-ol, is prepared from (S)-(−)-propylene oxide (commercially available from Aldrich Chemical Company) using a procedure analogous to that described for the preparation of (2R)-4-penten-2-ol from (R)-(+)-propylene oxide as reported by A. Kalivretenos, J. K. Stille, and L. S. Hegedus, *J. Org. Chem.* 56: 2883 (1991).

In another approach, such compounds as (3E)-N-methyl-4-(3-(6-aminopyridin)yl)-3-buten-1-amine can be prepared by subjecting a 3-halo-substituted pyridine such as 2-amino-5-bromopyridine (Aldrich Chemical Company) to a palladium-catalyzed coupling reaction with an olefin possessing a protected amine functionality, such as N-methyl-N-(3-buten-1-yl)benzamide. The benzoyl-protecting group from the resulting Heck reaction product can be removed by heating with aqueous acid to give (3E)-N-methyl-4-(3-(6-aminopyridin)yl)-3-buten-1-amine. The olefinic starting material, N-methyl-N-(3-buten-1-yl)benzamide, can be prepared by reacting 4-bromo-1-butene with an excess of condensed methylamine in N,N-dimethylformamide in the presence of potassium carbonate to give N-methyl-3-buten-1-amine. Treatment of the latter compound with benzoyl chloride in dichloromethane containing triethylamine affords the olefinic side chain, N-methyl-N-(3-buten-1-yl)benzamide.

The compounds described herein can contain a pyrazine or pyridazine ring. Using procedures reported M. Hasegawa, et al. (European Patent No. 0 516 409 B1), 2-methylpyrazine or 3-methylpyridazine (both available from Aldrich Chemical Company) can be condensed with N-methyl-N-(tert-butoxycarbonyl)-3-aminobutanal to give (4E)-N-methyl-N-(tert-butoxycarbonyl)-5-(2-pyrazinyl)-4-penten-2-amine and (4E)-N-methyl-N-(tert-butoxycarbonyl)-5-(3-pyridazinyl)-4-penten-2-amine, respectively. Removal of the tert-butoxycarbonyl group with trifluoroacetic acid will produce (4E)-N-methyl-5-(2-pyrazinyl)-4-penten-2-amine and (4E)-N-methyl-5-(3-pyridazinyl)-4-penten-2-amine, respectively. The requisite N-methyl-N-(tert-butoxycarbonyl)-3-aminobutanal can be produced from the corresponding alcohol using techniques described by M. Adamczyk and Y. Y. Chen in PCT International Application WO 9212122. The alcohol, N-methyl-N-(tert-butoxycarbonyl)-3-amino-1-butanol, can be made from commercially available 4-hydroxy-2-butanone (Lancaster Synthesis, Inc.) by sequential reductive amination (with methylamine and sodium cyanoborohydride, using chemistry reported by R. F. Borch in *Org. Syn.*, 52:124 (1974)) and protection with di-tert-butyl dicarbonate.

The Heck coupling reaction described above is also useful in preparing compounds that possess certain fused-ring heterocycles. Such compounds can be synthesized by the palladium-catalyzed coupling of a bromo heterocyclic compound, such as 6-bromo-2-methyl-1H-imidazo[4,5-b]pyridine with the previously mentioned olefinic amine side chain, N-methyl-N-(tert-butoxycarbonyl)-4-penten-2-amine. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an olefin and an aromatic halide are used for the coupling reaction. The resulting tert-butoxycarbonyl-protected (Boc-protected) intermediate can be subjected to treatment with a strong acid, such as trifluoroacetic acid to produce (4E)-N-methyl-5-(6-(2-methyl-1H-imidazo[4,5-b]pyridin)yl)-4-penten-2-amine. The requisite bromo-imidazopyridine, 6-bromo-2-methyl-1H-imidazo[4,5-b]pyridine can be prepared in 82% yield by heating 2,3-diamino-5-bromopyridine with acetic acid in polyphosphoric acid according to the methods described by P. K. Dubey et al., *Indian J. Chem.* 16B(6):531-533 (1978). 2,3-Diamino-5-bromopyridine can be prepared in 97% yield by heating 2-amino-5-bromo-3-nitropyridine (commercially available from Aldrich Chemical Company and Lancaster Synthesis, Inc) with tin(II) chloride dihydrate in boiling ethanol according to the techniques described by S. X. Cai et al., *J. Med. Chem.* 40(22): 3679-3686 (1997).

In another example, a bromo fused-ring heterocycle, such as 6-bromo-1,3-dioxolo[4,5-b]pyridine can be coupled with the previously mentioned olefinic amine side chain, N-methyl-N-(tert-butoxycarbonyl)-4-penten-2-amine using the Heck reaction. The resulting Boc-protected intermediate can be deprotected with a strong acid such as trifluoroacetic acid to produce (4E)-N-methyl-5-(6-(1,3-dioxolo[4,5-b]pyridin)yl)-4-penten-2-amine. The requisite bromo compound, 6-bromo-1,3-dioxolo[4,5-b]pyridine can be synthesized from 5-bromo-2,3-dihydroxypyridine, also known as 5-bromo-3-hydroxy-2(1H)-pyridinone, via a methylenation procedure using bromochloromethane, in the presence of potassium carbonate and N,N-dimethylformamide according to the methodology of F. Dallacker et al., *Z. Naturforsch.* 34 b:1729-1736 (1979). 5-Bromo-2,3-dihydroxypyridine can be prepared from furfural (2-furaldehyde, commercially available from Aldrich Chemical Company and Lancaster Synthesis, Inc.) using the methods described in F. Dallacker et al., *Z. Naturforsch.* 34 b:1729-1736 (1979). Alternatively, 5-bromo-2,3-dihydroxypyridine can be prepared according to the techniques described in EP 0081745 to D. Rose and N. Maak.

In another example of a compound that possesses a fused-ring heterocycle, the bromo compound, 7-bromo-2,3-dihydro-1,4-dioxino[2,3-b]pyridine (also known as 7-bromo-5-aza-4-oxachromane) can be condensed with the previously mentioned olefinic amine side chain, N-methyl-N-(tert-butoxycarbonyl)-4-penten-2-amine using the Heck reaction. The resulting Boc-protected compound can be deprotected with strong acid such as trifluoroacetic acid to produce (4E)-N-methyl-5-(7-(2,3-dihydro-1,4-dioxino[2,3-b]pyridin)yl-4-penten-2-amine. The bromo compound, 7-bromo-2,3-dihydro-1,4-dioxino[2,3-b]pyridine, can be prepared by treating 5-bromo-2,3-dihydroxypyridine with 1,2-dibromoethane and potassium carbonate in N,N-dimethylformamide according to the methodology of F. Dallacker et al., *Z. Naturforsch.* 34 b: 1729-1736 (1979). 5-Bromo-2,3-dihydroxypyridine can be prepared from furfural as described above.

Other polycyclic aromatic compounds can be prepared by the Heck reaction. Thus, certain compounds can be synthesized by the palladium-catalyzed coupling of a bromo fused-ring heterocycle, such as 6-bromo-1H-imidazo[4,5-b]pyridine-2-thiol with the previously mentioned olefinic amine side chain, N-methyl-N-(tert-butoxycarbonyl)-4-penten-2-amine. The Boc-protected intermediate, resulting from the Heck reaction, can be subjected to treatment with a strong acid, such as trifluoroacetic acid to produce (4E)-N-methyl-5-(6-(2-thio-1H-imidazo[4,5-b]pyridin)yl)-4-penten-2-amine. The requisite bromo compound, 6-bromo-1H-imidazo[4,5-b]pyridine-2-thiol can be prepared by treating 6-bromo-1H-imidazo[4,5-b]pyridine with sulfur at 230-260° C. according to the methods described in Y. M. Yutilov, *Khim. Geterotsikl Doedin.* 6: 799-804 (1988). 6-Bromo-1H-imidazo[4,5-b]pyridine can be obtained from Sigma-Aldrich Chemical Company. Alternatively, 6-bromo-1H-imidazo[4,5-b]pyridine can be prepared by treating 2,3-diamino-5-bromopyridine with formic acid in polyphosphoric acid using methodology similar to that described by P. K. Dubey et al., *Indian J. Chem.* 16B(6):531-533 (1978). 2,3-Diamino-5-bromopyridine can be prepared in 97% yield by heating 2-amino-5-bromo-3-nitropyridine (commercially available from Aldrich Chemical Company and Lancaster Synthesis, Inc) with tin(II) chloride dihydrate in boiling ethanol according to the techniques described by S. X. Cai et al., *J. Med. Chem.*, 40(22): 3679-3686 (1997). Alternatively, 6-bromo-1H-imidazo[4,5-b]pyridine-2-thiol can be prepared by heating 2,3-diamino-5-bromopyridine with $K^{+-}$ SCSOEt in aqueous ethanol using methodology similar to that described by T. C. Kuhler et al., *J. Med. Chem.* 38(25): 4906-4916 (1995). 2,3-Diamino-5-bromopyridine can be prepared from 2-amino-5-bromo-3-nitropyridine as described above.

In a related example, 6-bromo-2-phenylmethylthio-1H-imidazo[4,5-b]pyridine can be coupled via Heck reaction with the previously mentioned olefinic amine side chain, N-methyl-N-(tert-butoxycarbonyl)-4-penten-2-amine. The resulting Boc-protected intermediate can be subjected to treatment with a strong acid, such as trifluoroacetic acid to produce (4E)-N-methyl-5-(6-(2-phenylmethylthio-1H-imidazo[4,5-b]pyridin)yl)-4-penten-2-amine. The bromo compound, 6-bromo-2-phenylmethylthio-1H-imidazo[4,5-b]pyridine can be prepared by alkylating the previously described 6-bromo-1H-imidazo[4,5-b]pyridine-2-thiol with benzyl bromide in the presence of potassium carbonate and N,N-dimethylformamide.

In another example, 6-bromooxazolo[4,5-b]pyridine, when submitted sequentially to palladium catalyzed coupling to N-methyl-N-(tert-butoxycarbonyl)-4-penten-2-amine and deprotection with trifluoroacetic acid, gives (4E)-N-methyl-5-(6-oxazolo[4,5-b]pyridinyl)-4-penten-2-amine. The requisite 6-bromooxazolo[4,5-b]pyridine can be produced from 2-amino-5-bromo-3-pyridinol by condensation with formic acid or a trialkyl orthoformate, using methodology similar to that of M-C. Viaud et al., *Heterocycles* 41: 2799-2809 (1995). The use of other carboxylic acids produces 2-substituted-6-bromooxazolo[4,5-b]pyridines, which are also substrates for the Heck reaction. The synthesis of 2-amino-5-bromo-3-pyridinol proceeds from furfurylamine (Aldrich Chemical Company). Thus, 5-bromo-3-pyridinol (produced from furfurylamine according to U.S. Pat. No. 4,192,946) can be chlorinated, using methods described by V. Koch et al., *Synthesis*, 499 (1990), to give 2-chloro-5-bromo-3-pyridinol, which in turn can be converted to 2-amino-5-bromo-3-pyridinol by treatment with ammonia.

5-Bromooxazolo[5,4-b]pyridine, isomeric by orientation of ring fusion to the previously described 6-bromooxazolo[4,5-b]pyridine, can also be used in the Heck coupling with N-methyl-N-(tert-butoxycarbonyl)-4-penten-2-amine. Subsequent removal of the tert-butoxycarbonyl protecting group provides (4E)-N-methyl-5-(5-oxazolo[5,4-b]pyridinyl)-4-penten-2-amine. The 5-bromooxazolo[5,4-b]pyridine can be synthesized from 3-amino-5-bromo-2-pyridinol (3-amino-5-bromo-2-pyridone) by condensation with formic acid (or a derivative thereof) as described above. 3-Amino-5-bromo-2-pyridinol can be made by bromination (using techniques described by T. Batkowski, *Rocz. Chem.* 41: 729-741 (1967)) and subsequent tin(II) chloride reduction (according to the method described by S. X. Cai et al., *J. Med. Chem.* 40(22): 3679-3686 (1997)) of commercially available 3-nitro-2-pyridinol (Aldrich Chemical Company).

Other polycyclic aromatic compounds of the present invention can be prepared by the Heck reaction. Thus both 5-bromofuro[2,3-b]pyridine and 5-bromo-1H-pyrrolo[2,3-b]pyridine can undergo palladium catalyzed coupling with the previously described olefinic amine side chain, N-methyl-N-(tert-butoxycarbonyl)-4-penten-2-amine, to give (4E)-N-methyl-N-(tert-butoxycarbonyl)-5-(5-furo[2,3-b]pyridinyl)-4-penten-2-amine and (4E)-N-methyl-N-(tert-butoxycarbonyl)-5-(5-1H-pyrrolo[2,3-b]pyridinyl)-4-penten-2-amine respectively. Subsequent removal of the tert-butoxycarbonyl group with trifluoroacetic acid will provide (4E)-N-methyl-5-(5-furo[2,3-b]pyridinyl)-4-penten-2-amine and (4E)-N-methyl-5-(5-1H-pyrrolo[2,3-b]pyridinyl)-4-penten-2-amine. The requisite 5-bromofuro[2,3-b]pyridine and 5-bromo-1H-pyrrolo[2,3-b]pyridine can be made from 2,3-dihydrofuro[2,3-b]pyridine and 2,3-dihydropyrrolo[2,3-b]pyridine respectively, by bromination (bromine and sodium bicarbonate in methanol) and dehydrogenation (2,3-dichloro-5,6-dicyano-1,4-benzoquinone), using chemistry described by E. C. Taylor et al., *Tetrahedron* 43: 5145-5158 (1987). 2,3-Dihydrofuro[2,3-b]pyridine and 2,3-dihydropyrrolo[2,3-b]pyridine are, in turn, made from 2-chloropyrimidine (Aldrich Chemical Company), as described by A. E. Frissen et al., *Tetrahedron* 45: 803-812 (1989), by nucleophilic displacement of the chloride (with the sodium salt of 3-butyn-1-ol or with 4-amino-1-butyne) and subsequent intramolecular Diels-Alder reaction. Using similar chemistry, 2,3-dihydrofuro[2,3-b]pyridine and 2,3-dihydropyrrolo[2,3-b]pyridine are also produced from 3-methylthio-1,2,4-triazene (E. C. Taylor et al., *Tetrahedron* 43: 5145-5158 (1987)), which in turn is made from glyoxal and S-methylthiosemicarbazide (W. Paudler et al., *J. Heterocyclic Chem.* 7: 767-771 (1970)).

Brominated dihydrofuropyridines, dihydropyrrolopyridines, and dihydropyranopyridines are also substrates for the palladium catalyzed coupling. For instance, both 5-bromo-2,3-dihydrofuro[2,3-b]pyridine and 5-bromo-2,3-dihydropyrrolo[2,3-b]pyridine (from bromination of 2,3-dihydrofuro[2,3-b]pyridine and 2,3-dihydropyrrolo[2,3-b]pyridine, as described above) can be coupled with the previously mentioned olefinic amine side chain in a Heck process. Subsequent deprotection gives the corresponding (4E)-N-methyl-5-(5-(2,3-dihydrofuro[2,3-b]pyridin)yl)-4-penten-2-amine and (4E)-N-methyl-5-(5-(2,3-dihydropyrrolo[2,3-b]pyridin)yl)-4-penten-2-amine. Similar treatment of 6-bromo-2,3-dihydrofuro[3,2-b]pyridine (isomeric at the ring fusion with the [2,3-b]system) will provide (4E)-N-methyl-5-(6-(2,3-dihydrofuro[3,2-b]pyridin)yl)-4-penten-2-amine. The requisite 6-bromo-2,3-dihydrofuro[3,2-b]pyridine can be made from 5-bromo-2-methyl-3-pyridinol by sequential treatment with two equivalents of lithium diisopropylamide (to generate the 2-methylenyl, 3-oxy dianion) and one equivalent of dibromomethane. Alternatively, using chemistry similar to that described by M. U. Koller et al., *Synth. Commun.* 25: 2963-74 (1995), the silyl-protected pyridinol (5-bromo-2-methyl-3-trimethylsilyloxypyridine) can be treated sequentially with one equivalent of lithium diisopropylamide and an alkyl or aryl aldehyde to produce a 2-(2-(1-alkyl- or 1-aryl-1-hydroxy)ethyl)-5-bromo-3-(trimethylsilyloxy)pyridine. Such materials can be converted, by methods (such as acid catalyzed cyclization or the Williamson synthesis) known to those skilled in the art, into the corresponding cyclic ethers (2-alkyl- or 2-aryl-6-bromo-2,3-dihydrofuro[3,2-b]pyridines). Similar chemistry, in which epoxides (instead of aldehydes) are used in reaction with the pyridinylmethyl carbanion, leads to 2-alkyl- and 2-aryl-7-bromo-2,3-dihydropyrano[3,2-b]pyridines. These 2-substituted, brominated dihydrofuro- and dihydropyranopyridines are also substrates for the Heck reaction. For instance, 6-bromo-2,3-dihydro-2-phenylfuro[3,2-b]pyridine can be coupled, in a palladium catalyzed process, with N-methyl-N-(tert-butoxycarbonyl)-4-penten-2-amine, and the coupling product treated with trifluoroacetic acid (to remove the tert-butoxycarbonyl group), to give (4E)-N-methyl-5-(6-(2,3-dihydro-2-phenyl-furo[3,2-b]pyridin)yl)-4-penten-2-amine.

The 5-bromo-2-methyl-3-pyridinol, used to synthesize the brominated dihydrofuro- and dihydropyranopyridines, is produced by standard transformations of commercially available materials. Thus, 2-methylnicotinic acid (Aldrich Chemical Company) can be converted, by sequential treatment with thionyl chloride, bromine, and ammonia (methodology described by C. V. Greco et al., *J. Heterocyclic Chem.* 7: 761-766 (1970)), into 5-bromo-2-methylnicotinamide. Hofinann rearrangement of 5-bromo-2-methylnicotinamide with hypochlorite will give 3-amino-5-bromo-2-methylpyridine, which can be converted to 5-bromo-2-methyl-3-pyridinol by diazotization with sodium nitrite in aqueous sulfuric acid. Alternatively, alanine ethyl ester (Aldrich Chemical Company) is converted (using ethyl formate) into its N-formyl derivative, which is then converted to 5-ethoxy-4-methyloxazole using phosphorous pentoxide (N. Takeo et al., *Japan Patent No.* 45,012,732). Diels-Alder reaction of 5-ethoxy-4-methyloxazole with acrylonitrile gives 5-hydroxy-6-methylnicotinonitrile (T. Yoshikawa et al., *Chem. Pharm. Bull.* 13: 873 (1965)), which is converted to 5-amino-2-methyl-3-pyridinol by hydration and Hofinann rearrangement (Y. Morisawa et al., *Agr. Biol. Chem.* 39: 1275-1281 (1975)). The 5-amino-2-methyl-3-pyridinol can then be converted, by diazotization in the presence of cuprous bromide, to the desired 5-bromo-2-methyl-3-pyridinol.

These methods each provide the (E)-metanicotine-type compounds as the major product, but also produce a minor amount of the corresponding (Z)-metanicotine-type compounds and other isomers, as before described. These minor reaction products can be removed using conventional techniques, if desired. Alternatively, as described in more detail below, the (E)-metanicotine-type compounds can be isolated as the hydroxybenzoate salts, which can precipitate out in substantially pure form from a reaction mixture including hydroxybenzoate salts of the (Z)-metanicotine-type compounds and other minor reaction products.

Other methods beside the Heck coupling reaction can be used to provide the compounds. For example, the (E)-metanicotine-type compounds can be prepared using the techniques set forth by Loffler et al., *Chem. Ber.*, 42:3431-3438 (1909) and Laforge, *J.A.C.S.*, 50:2477 (1928) from substituted nicotine-type compounds. Certain 6-substituted metanicotine-type compounds can be prepared from the corresponding 6-substituted nicotine-type compounds using the general methods of Acheson et al., *J. Chem. Soc., Perkin Trans.* 1(2):579-585 (1980). The requisite precursors for such compounds, 6-substituted nicotine-type compounds, can be synthesized from 6-substituted nicotinic acid esters using the general methods disclosed by Rondahl, *Acta Pharm. Suec.*, 14:113-118 (1977). Preparation of certain 5-substituted metanicotine-type compounds can be accomplished from the corresponding 5-substituted nicotine-type compounds using the general method taught by Acheson et al., *J. Chem. Soc., Perkin Trans.* 1(2): 579-585 (1980). The 5-halo-substituted nicotine-type compounds (e.g., fluoro- and bromo-substituted nicotine-type compounds) and the 5-amino nicotine-type compounds can be prepared using the general procedures disclosed by Rondahl, *Act. Pharm. Suec.*, 14:113-118 (1977). The 5-trifluoromethyl nicotine-type compounds can be prepared using the techniques and materials set forth in Ashimori et al., *Chem. Pharm. Bull.*, 38(9):2446-2458 (1990) and Rondahl, *Acta Pharm. Suec.*, 14:113-118 (1977).

Formation of E-metanicotine Hydroxybenzoates

The (E)-metanicotine hydroxybenzoates are formed by reacting the E-metanicotine-type compounds described above with hydroxybenzoic acids. The stoichiometry of the individual components (E-metanicotine and hydroxybenzoic acid) used to prepare the salts can vary. It is typical that the molar ratio of hydroxybenzoic acid to base (E-metanicotine) is typically 2:1 to 1:2, more typically 2:1 or 1:1, but other ratios (such as 3:2) are possible. It is preferred that the molar ratio of acid to base is 1:1. Depending upon the manner by which the salts of the present invention are formed, those salts may have crystal structures that may occlude solvents that are present during salt formation. Thus, salts of the present invention can occur as hydrates and other solvates of varying stoichiometry of solvent relative to aryl substituted amine.

The method for providing compounds of the present invention can vary. For instance, the preparation of (2S)-(4E)-N-methyl-5-(5-isopropoxy-3-pyridinyl)-4-penten-2-amine in a p-hydroxybenzoate form can involve (i) adding a solution of suitably pure compound dissolved in ethanol to a solution of p-hydroxybenzoic acid (1-1 equivalents) in ethanol, heated under reflux, to form a precipitate, (ii) applying heat and/or water and ethanol (water not to exceed 10%) to dissolve the precipitate, (iii) cooling the resulting solution if necessary to cause precipitation of the salt and (iv) filtering and collecting the salt. The stoichiometry, solvent mix, solute concentration and temperature employed can vary, but the formation of the salts is within the level of skill of those of skill in the art.

Formation of Other Salt Forms

If desired, once the hydroxybenzoate salts are isolated, other salt forms can be formed, for example, by direct reaction with another pharmaceutically acceptable acid or by first isolating the free base (by reaction with strong base and extraction into an appropriate solvent) and then reaction with another pharmaceutically acceptable acid. Such procedures are known to those of skill in the art.

III. Pharmaceutical Compositions

The pharmaceutical compositions of the present invention include the hydroxybenzoates described herein, in the pure state or in the form of a composition in which the compounds are combined with any other pharmaceutically compatible product, which can be inert or physiologically active. Such compositions can be administered, for example, orally, parenterally, rectally, or topically.

Examples of solid compositions for oral administration include, but are not limited to, tablets, pills, powders (gelatin capsules, cachets), and granules. In these compositions, the active compound is mixed with one or more inert diluents, such as starch, cellulose, sucrose, lactose, or silica; ideally, under a stream of an inert gas such as argon.

The compositions can also include substances other than diluents, for example, one or more lubricants such as magnesium stearate or talc, a colorant, a coating (coated tablets), or a varnish.

Examples of liquid compositions for oral administration include, but are not limited to, solutions, suspensions, emulsions, syrups, and elixirs that are pharmaceutically acceptable and typically contain inert diluents such as water, ethanol, glycerol, vegetable oils, or liquid paraffin. These compositions can comprise substances other than the diluents, for example, wetting agents, sweeteners, thickeners, flavors, and stabilizers.

Sterile compositions for parenteral administration can include, for example, aqueous or nonaqueous solutions, suspensions, and emulsions. Examples of suitable solvents and vehicles include, but are not limited to aqueous solutions, preferably buffered aqueous solutions, propylene glycol, a polyethylene glycol, vegetable oils, especially olive oil, injectable organic esters, for example ethyl oleate, and other appropriate organic solvents. These compositions can also include adjuvants, especially wetting agents, isotonicity agents, emulsifiers, dispersants, and stabilizers. Such sterile compositions can be sterilized in a number of ways, for example, by asepticizing filtration, by incorporating sterilizing agents into the composition, by irradiation and by heating. They can also be prepared in the form of sterile solid compositions which can be dissolved at the time of use in sterile water or any other sterile injectable medium.

Examples of compositions for rectal administration include, but are not limited to, suppositories and rectal capsules that, in addition to the active product, can include excipients such as cocoa butter, semi-synthetic glycerides, and polyethylene glycols.

Compositions for topical administration can, for example, be creams, lotions, eyewashes, collutoria, nasal drops or aerosols.

The pharmaceutical compositions also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, anticoagulants, buffering agents, anti-inflammatory agents, antipyretics, time release binders, anesthetics, steroids, and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular disorder.

IV. Methods of Treatment

The hydroxybenzoate salts described herein are useful for treating those types of conditions and disorders for which other types of nicotinic compounds have been proposed as therapeutics. See, for example, Williams et al., *DN&P* 7(4): 205-227 (1994); Arneric et al., *CNS Drug Rev.* 1(1):1-26 (1995); Americ et al., *Exp. Opin. Invest. Drugs* 5(1):79-100 (1996); Bencherif et al., *J. Pharmacol. Exp. Ther.* 279:1413 (1996); Lippiello et al., *J. Pharmacol. Exp. Ther.* 279:1422 (1996); Damaj et al., *Neuroscience* (1997); Holladay et al., *J. Med. Chem.* 40(28): 4169-4194 (1997); Bannon et al., *Science* 279: 77-80 (1998); PCT WO 94/08992; PCT WO 96/31475; and U.S. Pat. No. 5,583,140 to Bencherif et al.; U.S. Pat. No. 5,597,919 to Dull et al.; and U.S. Pat. No. 5,604,231 to Smith et al.

The salts can also be used as adjunct therapy in combination with existing therapies in the management of the aforementioned types of diseases and disorders. In such situations, it is preferably to administer the active ingredients in a manner that minimizes effects upon nAChR subtypes such as those that are associated with muscle and ganglia. This can be accomplished by targeted drug delivery and/or by adjusting the dosage such that a desired effect is obtained without meeting the threshold dosage required to cause significant side effects. The pharmaceutical compositions can be used to ameliorate any of the symptoms associated with those conditions, diseases, and disorders.

Examples of conditions and disorders that can be treated include neurological disorders, neurodegenerative disorders, in particular, CNS disorders, and inflammatory disorders. CNS disorders can be drug induced; can be attributed to genetic predisposition, infection or trauma; or can be of unknown etiology. CNS disorders comprise neuropsychiatric disorders, neurological diseases, and mental illnesses, and include neurodegenerative diseases, behavioral disorders, cognitive disorders, and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of choline, dopamine, norepinephrine, and/or serotonin.

Examples of CNS disorders that can be treated using the E-metanicotine compounds and hydroxybenzoate salts described herein, and pharmaceutical compositions including these compounds and salts, include pre-senile dementia (early onset Alzheimer's disease), senile dementia (dementia of the Alzheimer's type), Lewy Body dementia, micro-infarct dementia, AIDS-related dementia, HIV-dementia, multiple cerebral infarcts, Parkinsonism including Parkinson's disease, Pick's disease, progressive supranuclear palsy, Huntington's chorea, tardive dyskinesia, hyperkinesia, epilepsy, mania, attention deficit disorder, anxiety, depression, dyslexia, schizophrenia depression, obsessive-compulsive disorders, Tourette's syndrome, mild cognitive impairment (MCI), age-associated memory impairment (AAMI), premature amnesic and cognitive disorders which are age-related or a consequence of alcoholism, or immunodeficiency syndrome, or are associated with vascular disorders, with genetic alterations (such as, for example, trisomy 21) or with attention deficiencies or learning deficiencies, acute or chronic neurodegenerative conditions such as amyotrophic lateral sclerosis, multiple sclerosis, peripheral neurotrophies, and cerebral or spinal traumas. In addition, the compounds can be used to treat nicotine addiction and/or other behavioral disorders related to substances that lead to dependency (e.g., alcohol, cocaine, heroin and opiates, psychostimulants, benzodiazepines, and barbiturates), and to treat obesity. The compounds can also be used to treat pathologies exhibiting an inflammatory character within the gastrointestinal system such as Crohn's disease, irritable bowel syndrome and ulcerative colitis, and diarrheas.

The manner in which the hydroxybenzoate salts are administered can vary. The salts can be administered by inhalation (e.g., in the form of an aerosol either nasally or using delivery articles of the type set forth in U.S. Pat. No. 4,922,901 to Brooks et al.); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebroventricularly; or transdermally (e.g., using a transdermal patch). Although it is possible to administer the salts in the form of a bulk active chemical, it is preferred to present each salts in the form of a pharmaceutical composition or formulation for efficient and effective administration. Exemplary methods for administering such salts will be apparent to the skilled artisan. For example, the salts can be administered in the form of a tablet, a hard gelatin capsule or as a time-release capsule. As another example, the salts can be delivered transdermally using the types of patch technologies available from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, or monkey); but, advantageously, the compounds are preferably administered to a human being. In addition, the time of day and the number of times per day that the pharmaceutical formulation is administered can vary. Administration preferably is such that the active ingredients of the pharmaceutical formulation interact with receptor sites within the body of the subject that affect the functioning of the CNS or of the gastrointestinal (GI) tract. More specifically, in treating a CNS disorder administration preferably is such so as to optimize the effect upon those relevant receptor subtypes which have an effect upon the functioning of the CNS, while minimizing the effects upon muscle-type receptor subtypes. Other suitable methods for administering the salts are described in U.S. Pat. No. 5,604,231 to Smith et al., the disclosure of which is incorporated herein by reference in its entirety.

The appropriate dose of the salts is that amount effective to prevent occurrence of the symptoms of the disorder or to treat some symptoms of the disorder from which the patient suffers. By "effective amount," "therapeutic amount," or "effective dose" is meant that amount sufficient to elicit the desired pharmacological or therapeutic effects, thus resulting in effective prevention or treatment of the disorder. Thus, when treating a CNS disorder, an effective amount of the hydroxybenzoate salts is an amount required to deliver, across the blood-brain barrier of the subject, a sufficient amount of the free base drug to bind to relevant receptor sites in the brain of the subject, and to modulate relevant nicotinic receptor subtypes (e.g., provide neurotransmitter secretion, thus resulting in effective prevention or treatment of the disorder). Prevention of the disorder is manifested by at least delaying the onset of the symptoms of the disorder or reducing the severity of the symptoms. Treatment of the disorder is manifested by a decrease in the symptoms associated with the disorder or an amelioration of the recurrence of the symptoms of the disorder.

The effective dose can vary, depending upon factors such as the condition of the patient, the severity of the symptoms of the disorder, and the manner in which the pharmaceutical composition is administered. For human patients, the effective dose of typical salts generally requires administering the salts in an amount sufficient to modulate relevant receptors to affect neurotransmitter (e.g., dopamine) release but the amount should be insufficient to induce effects on skeletal muscles and ganglia to any significant degree. The effective dose of the hydroxybenzoate salts will of course differ from patient to patient but in general includes amounts starting where CNS effects or other desired therapeutic effects occur, but below the amount where muscular effects are observed.

The doses depend on the desired effect, the duration of treatment and the administration route used; they are generally between 0.05 mg and 100 mg of active substance per day orally for an adult. Generally speaking, a medical doctor will determine the appropriate dosage as a function of the age, weight and all the other factors specific to the patient.

The salts of the present invention, when employed in effective amounts in accordance with the method of the present invention, often lack the ability to elicit activation of human ganglion nAChRs to any significant degree. This selectivity of the salts of the present invention against those nAChRs responsible for cardiovascular side effects is demonstrated by a lack of the ability of those salts to activate nicotinic function of adrenal chromaffin tissue. As such, such salts have poor ability to cause isotopic rubidium ion flux through nAChRs in cell preparations derived from the adrenal gland. Generally, typical preferred salts useful in carrying out the present invention maximally activate isotopic rubidium ion flux by less than 10 percent, often by less than 5 percent, of that maximally provided by S(−) nicotine.

The salts are effective towards providing some degree of prevention of the progression of CNS disorders, ameliorating the symptoms of CNS disorders, and ameliorating to some degree the recurrence of CNS disorders. However, such effective amounts of those salts are not sufficient to elicit any appreciable undesired nicotinic effects, as is demonstrated by decreased effects on preparations believed to reflect effects on the cardiovascular system, or effects to skeletal muscle. As such, administration of salts of the present invention provides a therapeutic window in which treatment of certain CNS disorders is provided, and undesired peripheral nicotinic effects/side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of CNS disorders occurs upon administration of less than $\frac{1}{3}$, frequently less than $\frac{1}{5}$, and often less than $\frac{1}{10}$, that amount sufficient to cause any side effects to a significant degree.

The following synthetic and analytical examples are provided to illustrate the present invention, and should not be construed as limiting thereof. In these examples, all parts and percentages are by weight, unless otherwise noted. Reaction yields are reported in mole percentages.

EXAMPLE 1

Synthesis of (2S)-(4E)-N-methyl-5-(5-isopropoxy-3-pyridinyl)-4-penten-2-amine p-hydroxybenzoate (2S)-(4E)-N-methyl-5-(5-isopropoxy-3-pyridinyl)-4-penten-2-amine p-hydroxybenzoate p-Hydroxybenzoic acid (2.62 g, 19.0 mmol) was added in portions to a stirred solution (2S)-(4E)-N-methyl-5-(5-isopropoxy-3-pyridinyl)-4-penten-2-amine (4.79 g of 93% pure, 19.0 mmol) in isopropyl acetate (50 mL). During the addition, crystallization of salt was evident. After complete addition of the p-hydroxybenzoic acid, the suspension was heated near its boiling point as isopropanol was slowly added. After 15 mL of isopropanol had been added, complete dissolution was obtained. Cooling of the solution to ambient temperature (overnight) resulted in deposition of a crystalline mass, which was collected by suction filtration and air dried (4.03 g). A second crop (0.82 g) was isolated from the concentrated filtrate, by addition of acetone. The two crops of crystals were combined and recrystallized from acetone (50 mL). The solid was collected by suction filtration and dried in the vacuum oven (50° C.) for 18 h. This left 4.24 g (60.0%) of white crystals (98+% pure by both GCMS and LCMS; m.p. 99-101° C.).

EXAMPLE 2

Synthesis of (2S)-(4E)-N-methyl-5-(5-isopropoxy-3-pyridinyl)-4-penten-2-amine (Via the Heck Reaction with (S)-N-Methyl-N-(tert-butoxycarbonyl)-4-penten-2-amine) and the Use of the p-hydroxybenzoate salt to Facilitate Isolation and Purification of (2S)-(4E)-N-methyl-5-(5-isopropoxy-3-pyridinyl)-4-penten-2-amine:

3-Bromo-5-isopropoxypyridine

A 72 L reactor was charged successively with sodium tert-pentoxide (2.2 kg, 20 mol) and 1-methyl-2-pyrrolidinone (17.6 L). This mixture was stirred for 1 h, and then 2-propanol (12 L) was added over a period of 2 h. 3,5-Dibromopyridine (3.0 kg, 13 mol) was then added to the reactor, and the mixture was heated at 75° C. for 12 h under a nitrogen atmosphere. The mixture was then cooled, diluted with toluene (15 L), and washed with water (30 L). The aqueous phase was extracted with toluene (15 L), and the combined toluene phases were washed with water (15 L) and concentrated under reduced pressure, to give 2.5 kg of dark oil. This was combined an equal sized batch of material from a second run and vacuum distilled (b.p. 65° C. at 0.3 mm), to yield 3.1 kg (57%) of 3-bromo-5-isopropoxypyridine as a pale yellow oil.

(2R)-4-Penten-2-ol (2R)-4-Penten-2-ol was prepared in 82.5% yield from (R)-(+)-propylene oxide according to procedures set forth in A. Kalivretenos, J. K. Stille, and L. S. Hegedus, *J. Org. Chem.* 56: 2883 (1991).

(S)-N-Methyl-N-(tert-butoxycarbonyl)-4-penten-2-amine

A mixture of (R)-4-penten-2-ol (7.62 g, 88.5 mmol), pyridine (15 mL), and dry (distilled from calcium hydride) dichloromethane (30 mL) was stirred in an ice bath as p-toluenesulfonyl chloride (18.6 g, 97.4 mmol) was added over a 3 min period. The mixture was stirred 20 min at 0° C. and 16 h at ambient temperature, as a heavy precipitate formed. Saturated aqueous sodium bicarbonate (75 mL) was added, and the biphasic mixture was stirred vigorously for 3 h. The dichloromethane phase and two dichloromethane extracts (50 mL each) of the aqueous phase were combined, dried ($Na_2SO_4$), and concentrated by rotary evaporation. High vacuum treatment left 18.7 g of light yellow oil, which was combined with dimethylformamide (DMF) (35 mL) and 40% aqueous methylamine (35 mL). This solution was stirred at ambient temperature for 48 h and then poured into a mixture of saturated aqueous sodium chloride (300 mL) and 2.5 M sodium hydroxide (50 mL). This mixture was extracted with ether (5×250 mL), and the ether extracts were dried ($Na_2SO_4$) and concentrated by rotary evaporation (from an ice cooled bath) to a volume of about 250 mL. The remaining solution was combined with di-tert-butyl dicarbonate (16.9 g, 77.4 mmol) and THF (100 mL), and the mixture was stirred at ambient temperature for 16 h. The volatiles were evaporated by rotary evaporation, and the residue was vacuum distilled at 5 mm pressure (bp 79-86° C.), to give 7.74 g (43.9% yield) of clear, colorless liquid.

(2S)-(4E)-N-Methyl-5-(5-isopropoxy-3-pyridinyl)-4-penten-2-amine p-hydroxybenzoate A mixture of 3-bromo-5-isopropoxypyridine (21.0 g, 97.2 mmol), (S)-N-Methyl-N-(tert-butoxycarbonyl)-4-penten-2-amine (24.0 g, 120 mmol), DMF (53 mL), $K_2CO_3$ (22 g, 159 mmol), palladium(II) acetate (0.22 g, 0.98 mmol) and tri-o-tolylphosphine (0.57 g, 1.9 mmol) was degassed and placed under a nitrogen atmosphere. The stirred mixture was then heated at 130° C. for 2.5 h. To remove palladium salts, Smopex™ (20 g) and ethyl acetate (100 mL) were added. The stirred mixture was heated at 50° C. for 5 h and at ambient temperature for 16 h and then filtered. The filtrate was concentrated under reduced pressure, and the residue (83 g) was dissolved in methanol (25 mL), cooled in a cold water bath (<5° C.) and treated drop-wise with 6 M HCl (100 mL). This mixture was stirred 3 h at ambient temperature, and the methanol was removed by concentration under vacuum. The remaining aqueous mixture was washed with dichloromethane (100 mL), made basic by careful (with cooling) addition of 3 M NaOH, and extracted (2×200 mL) with dichloromethane. These latter extracts were washed with saturated aqueous NaCl and concentrated under vacuum. The residue was dissolved in acetone (150 mL), and p-hydroxybenzoic acid (14.0 g, 101 mmol) was added. After complete dissolution of the p-hydroxybenzoic acid, the solution was kept at ambient temperature, as a large amount of solid formed (several hours). After several hours of cooling at −15° C., the mixture was suction filtered. The resulting solid (24.8 g) was recrystallized from acetone (240 mL) to give 22.3 g (61.6%) of off-white crystals (97+% pure by GCMS and LCMS).

EXAMPLE 3

Synthesis of (2S)-(4E)-N-methyl-5-(5-methoxy-3-pyridinyl)-4-penten-2-amine 2,5-dihydroxybenzoate (gentisate)

(2S)-(4E)-N-Methyl-5-(5-methoxy-3-pyridinyl)-4-penten-2-amine 2,5-dihydroxybenzoate A hot solution of 2,5-dihydroxybenzoic acid (gentisic acid) (0.582 g, 3.78 mmol) in absolute ethanol (1 mL) was added to a warm solution of (2S)-(4E)-N-methyl-5-(5-methoxy-3-pyridinyl)-4-penten-2-amine (1.00 g, 4.85 mmol, 86.7% E isomer by GC-FID) in absolute ethanol (1 mL), using additional ethanol (2 mL) in the transfer. The resulting mixture was concentrated via rotary evaporation, leaving 1.5 mL of ethanol in the solution. With stirring and heating to near reflux, crystallization occurred. The resulting hot mixture was treated drop-wise with ethyl acetate (5.5 mL). After cooling to room temperature, the mixture was further cooled at 5° C. for 48 h. The resulting solids were filtered, washed with ethyl acetate (2×5 mL) and dried at 50° C. to give 1.24 g (91%) of an off-white powder (98.0% E isomer by GC-FID for the free base). To remove the color from the sample, the material was recrystallized from ethanol/isopropanol (3.5 mL: 5.5 mL) to give 1.03 g (83% recovery) of an off-white powder and subsequently recrystallized from ethanol/ethyl acetate (3 mL:12 mL) to give 0.90 g (87% recovery) of a white, crystalline powder, mp 166-167° C.

EXAMPLE 4

Synthesis of E-metanicotine 2,5-dihydroxybenzoate

E-Metanicotine 2,5-dihydroxybenzoate 2,5-Dihydroxybenzoic acid (gentisic acid) (0.475 g, 3.08 mmol) was added to a solution of E-metanicotine (0.500 g, 3.08 mmol) in ethyl acetate (3 mL) and isopropanol (2.5 mL), and the resulting mixture was gently heated until all solids dissolved. Upon cooling, a white granular precipitate was deposited, and the mixture was cooled at 5° C. The solids were filtered, washed with cold isopropanol (3×2 mL) and dried under vacuum at 40° C. for 4 h to give 0.58 g (29.7%) of a light-yellow, flaky solid, mp 90-91.5° C. $^1$H NMR ($D_2O$): mono-salt stoichiometry. Calcd. for $C_{10}H_{14}N_2 \cdot C_7H_6O_4 \cdot 0.15H_2O$: C, 64.00%; H, 6.41%; N, 8.78%. Found: C, 63.92, 64.00%; H, 6.33, 6.34%; N, 8.79, 8.84%.

EXAMPLE 5

Synthesis of E-metanicotine 3,5-dihydroxybenzoate

E-Metanicotine 3,5-dihydroxybenzoate 5

3,5-Dihydroxybenzoic acid (0.475 g, 3.08 mmol) was added to a warm solution of E-metanicotine (0.500 g, 3.08 mmol) in isopropanol (11 mL) and methanol (4.5 mL). Upon heating to near reflux to dissolve the resulting gum, the light-yellow solution was cooled to room temperature and further cooled at 5° C. The resulting dark-yellow gum that was deposited was dissolved in isopropyl acetate (3 mL) and methanol (4 mL), assisted by heating. After cooling to room temperature and further cooling at 5° C., the off-white solids were filtered, washed with isopropyl acetate and dried to give 0.505 g (51.8%) of waxy, tan flakes, mp 160-161.5° C. $^1$H NMR ($D_2O$): mono-salt stoichiometry. Calcd. for $C_{10}H_{14}N_2 \cdot C_7H_6O_4 \cdot 0.15H_2O$: C, 64.00%; H, 6.41%; N, 8.78%. Found: C, 64.03, 64.02%; H, 6.38, 6.38%; N, 8.80, 8.76%.

ANALYTICAL EXAMPLES

EXAMPLE 6

Determination of Binding to Relevant Receptor Sites

The interaction of the hydroxybenzoate salts with relevant receptor sites can be determined in accordance with the techniques described in U.S. Pat. No. 5,597,919 to Dull et al. Inhibition constants (Ki values), reported in nM, can be calculated from the $IC_{50}$ values using the method of Cheng et al., *Biochem, Pharmacol.* 22:3099 (1973). Low binding constants indicate that the components of the salts described herein exhibit good high affinity binding to certain CNS nicotinic receptors.

The foregoing is illustrative of the present invention and is not to be construed as limiting thereof. The invention is defined by the following claims, with equivalents of the claims to be included therein.

What is claimed is:

1. A process for preparing (2S)-(4E)-N-methyl-5-(5-isopropoxy-3-pyridinyl)-4-penten-2-amine or a corresponding hydroxybenzoate salt, comprising the steps of:
   a) performing a Heck coupling reaction between a 3-halo-5-isopropoxypyridine and a compound of the formula (S)—$CH_2$=CH—($CH_2$)—CH($CH_3$)—N($CH_3$)(pg), where pg is a protecting group for an amine, and
   b) deprotecting the protected amine group, or
   c) performing a Heck coupling reaction between a 3-halo-5-isopropoxypyridine and a compound of the formula (R)—$CH_2$=CH—($CH_2$)—CH($CH_3$)—OH and
   d) converting the OH group to an $NHCH_3$ group, to form a mixture of compounds including (2S)-(4E)-N-methyl-5-(5-isopropoxy-3-pyridinyl)-4-penten-2-amine, the related Z-metanicotine compound, and other isomers,
   e) forming a hydroxybenzoate salt by reaction of the mixture with a hydroxybenzoic acid of the formula:

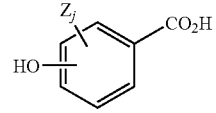

where the hydroxy group can be present at a position ortho, meta or para to the carboxylic acid group, Z represents a non-hydrogen substituent selected from the group consisting of alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, NR'R", $CF_3$, CN, $NO_2$, $C_2$ R', SH, $SCH_3$, $N_3$, $SO_2$ $CH_3$, OR', (CR'R")$_q$, OR', O—(CR'R")$_q$ $C_2$ R', SR', C(=O)NR'R", NR'C(=O)R", C(=O)R', C(=O)OR', OC(=O)R', (CR'R")$_q$, $OCH_2$ $C_2$ R', (CR'R")$_q$ C(=O)R', (CR'R")$_q$ C(CHCH$_3$)OR', O(CR'R")$_q$ C(=O)OR', (CR'R")$_q$, C(=O)NR'R", (CR'R")$_q$, NR'R", CH=CHR', OC(=O)NR'R", and NR'C(=O)OR", where q is an integer from 1 to 6 and R' and R" are individually hydrogen, $C_{1-10}$ alkyl, cycloalkyl, a non-aromatic heterocyclic ring wherein the heteroatom of the heterocyclic moiety is separated from any other nitrogen, oxygen or sulfur atom by at least two carbon atoms, or an aromatic group-containing species selected from the group consisting of pyridinyl, quinolinyl, pyrimidinyl, furanyl, phenyl, and benzyl, where any of the foregoing can be suitably substituted with at least one substituent group, such as alkyl, hydroxyl, alkoxyl, halo, or amino substituents, and j is a number from zero to three, representing the number of Z substituents that can be present on the ring, wherein the molar ratio of the E-metanicotine to hydroxybenzoic acid ranges from 1:2 to 2:1, f) isolating the (2S)-(4E)-N-methyl-5-(5-isopropoxy-3-pyridinyl)-4-penten-2-amine hydroxybenzoate salt, and g) optionally converting the (2S)-(4E)-N-methyl-5-(5-isopropoxy-3-pyridinyl)-4-penten-2-amine hydroxybenzoate salt to (2S)-(4E)-N-methyl-5-(5-isopropoxy-3-pyridinyl)-4-penten-2-amine.

2. The method of claim 1, wherein the hydroxybenzoic acid is o-, m- or p-hydroxybenzoic acid.

3. The method of claim 1 or 2, wherein the hydroxybenzoate salt is converted to another pharmaceutically acceptable salt form.

* * * * *